US012290376B2

(12) United States Patent
Murphy et al.

(10) Patent No.: US 12,290,376 B2
(45) Date of Patent: May 6, 2025

(54) SKIN INSPECTION DEVICE FOR IDENTIFYING ABNORMALITIES

(71) Applicant: Bluedrop Medical Limited, Galway (IE)

(72) Inventors: Christopher Murphy, Mayo (IE); Gavin Corley, Galway (IE); Simon Kiersey, Galway (IE)

(73) Assignee: BLUEDROP MEDICAL LIMITED, Galway (IE)

( * ) Notice: Subject to any disclaimer, the term of this patent is extended or adjusted under 35 U.S.C. 154(b) by 783 days.

(21) Appl. No.: 16/303,296

(22) PCT Filed: Apr. 6, 2017

(86) PCT No.: PCT/EP2017/058297
§ 371 (c)(1),
(2) Date: Nov. 20, 2018

(87) PCT Pub. No.: WO2017/202535
PCT Pub. Date: Nov. 30, 2017

(65) Prior Publication Data
US 2019/0209076 A1     Jul. 11, 2019

(30) Foreign Application Priority Data
May 23, 2016 (GB) ..................... 1609031

(51) Int. Cl.
*A61B 5/00* (2006.01)
*A61B 5/01* (2006.01)
(Continued)

(52) U.S. Cl.
CPC ............ *A61B 5/445* (2013.01); *A61B 5/0022* (2013.01); *A61B 5/0077* (2013.01); *A61B 5/015* (2013.01);
(Continued)

(58) Field of Classification Search
None
See application file for complete search history.

(56) References Cited

U.S. PATENT DOCUMENTS 3,965,742 A * 6/1976 Parker ..................... G01K 1/028
374/161
4,195,561 A * 4/1980 Castanis .............. A23C 9/1226
116/216
(Continued)

FOREIGN PATENT DOCUMENTS

FR        2516779        *  5/1983
JP        2006010320 A   *  1/2006
WO        2016025430 A1     2/2016

OTHER PUBLICATIONS

Bharara M. Liquid crystal thermography for neuro-pathic assessment of the diabetic foot. PhD Thesis. Bournemouth University, Bouremouth, 2007 (Year: 2007).*
(Continued)

*Primary Examiner* — Matthew Kremer
(74) *Attorney, Agent, or Firm* — Tarolli, Sundheim, Covell & Tummino LLP

(57) ABSTRACT

A skin inspection device for identifying abnormalities; the device comprising: a transparent panel having an inspection area; an array of thermochromic liquid crystal (TLC) formations provided on the transparent panel which are operable to change colour in response to a change of temperature; and one or more image capture devices for capturing a colour image of the TLC formations and an area of skin of a target located in the inspection area; the captured colour image being analysed to identify abnormalities in the area of skin.

51 Claims, 21 Drawing Sheets

(51) Int. Cl.
    *A61B 5/103*     (2006.01)
    *G01G 19/50*     (2006.01)
    *G02F 1/13*     (2006.01)

(52) U.S. Cl.
    CPC .......... *A61B 5/1032* (2013.01); *A61B 5/1036* (2013.01); *A61B 5/441* (2013.01); *A61B 5/442* (2013.01); *A61B 5/443* (2013.01); *A61B 5/447* (2013.01); *A61B 5/7203* (2013.01); *A61B 5/7235* (2013.01); *A61B 5/746* (2013.01); *G01G 19/50* (2013.01); *G02F 1/132* (2013.01); *A61B 5/444* (2013.01); *A61B 2560/0223* (2013.01); *A61B 2562/0261* (2013.01); *A61B 2562/0271* (2013.01); *A61B 2562/0276* (2013.01); *A61B 2562/046* (2013.01); *A61B 2562/185* (2013.01); *A61B 2576/02* (2013.01)

(56) References Cited

U.S. PATENT DOCUMENTS

| | | | | |
|---|---|---|---|---|
| 4,524,778 | A * | 6/1985 | Brown, Jr. | A61B 5/4312 |
| | | | | 600/549 |
| 2002/0082486 | A1 | 6/2002 | Lavery | |
| 2007/0211355 | A1 | 9/2007 | Dalbo | |
| 2008/0109183 | A1 * | 5/2008 | Shoureshi | A61B 5/01 |
| | | | | 702/131 |
| 2013/0261494 | A1 * | 10/2013 | Bloom | A61B 5/7282 |
| | | | | 600/549 |
| 2014/0121479 | A1 * | 5/2014 | O'Connor | A61B 5/447 |
| | | | | 600/306 |
| 2015/0133792 | A1 * | 5/2015 | Spahn | A61B 5/7425 |
| | | | | 600/474 |
| 2015/0323388 | A1 * | 11/2015 | Kostic | A61G 7/0528 |
| | | | | 250/338.1 |
| 2016/0058299 | A1 * | 3/2016 | Hsiao | A61B 5/447 |
| | | | | 600/549 |
| 2017/0224257 | A1 * | 8/2017 | Rogers | A61B 5/0537 |

OTHER PUBLICATIONS

English translation of FR2516779, www.patents.google.com, 4 pages, printed on May 9, 2022 (Year: 2022).*

English machine translation of JP-2006010320-A, Clarivate Analytics, 9 pages, printed on May 3, 2023 (Year: 2023).*

"Substantial." Merriam-Webster.com Dictionary, Merriam-Webster, www.merriam-webster.com/dictionary/substantial. Accessed Jul. 21, 2024. (Year: 2024).*

International Search Report and Written Opinion for corresponding International Application No. PCT/EP2017/058297, dated Jun. 22, 2017.

* cited by examiner

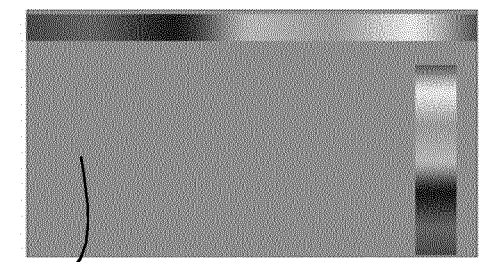
102   Fig. 14
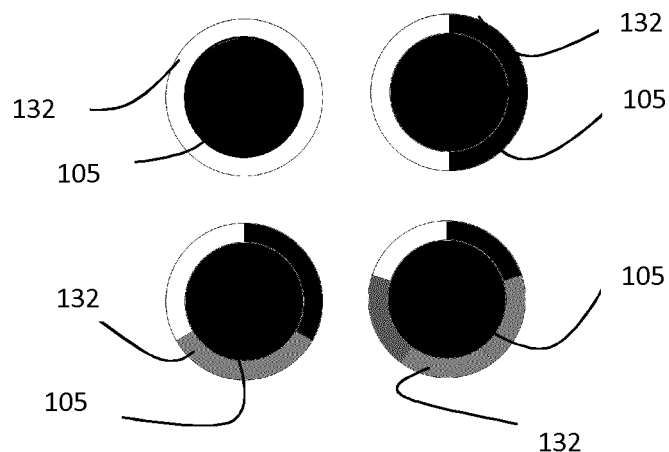
Fig. 15
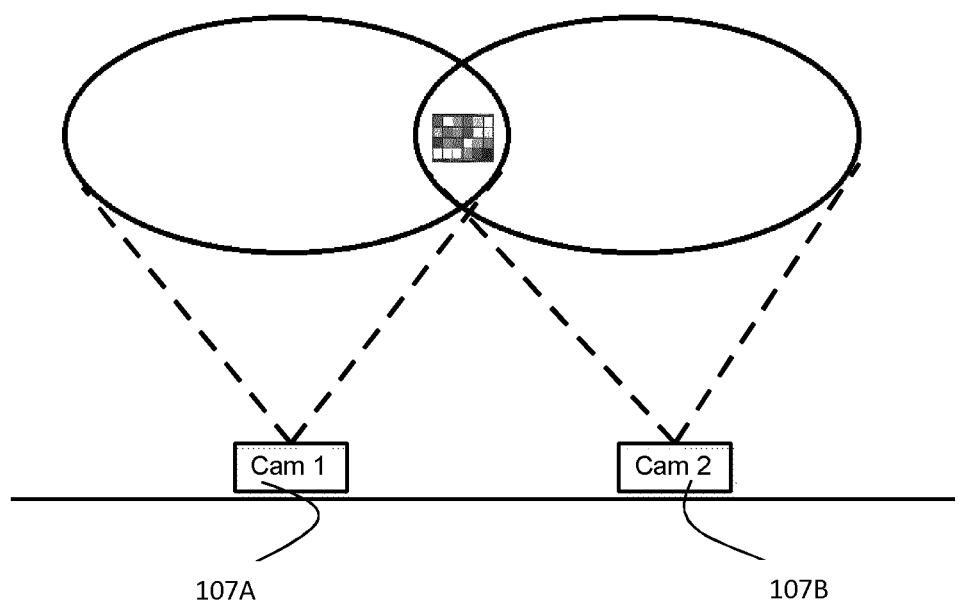
107A   Fig. 16   107B

SKIN INSPECTION DEVICE FOR IDENTIFYING ABNORMALITIES

RELATED APPLICATIONS

The present invention is a U.S. National Stage under 35 USC 371 patent application, claiming priority to Serial No. PCT/EP2017/058297, filed on 6 Apr. 2017; which claims priority of GB 1609031.8, filed on 23 May 2016, the entirety of both of which are incorporated herein by reference.

FIELD OF THE INVENTION

The present disclosure relates to a skin inspection device for identifying abnormalities. In particular, but not exclusively, the skin inspection device relates to heat sensing a sole of a human foot in order to predict the formation of ulcers.

BACKGROUND

Diabetics commonly suffer from a condition known as diabetic foot ulcers (DFU) over their lifetime. It is recommended that diabetics inspect their feet daily so as detect any abnormal damage to the skin that may be an indicator of the onset of DFU. However, limiting factors such as reduced vision, reduced mobility, lack of sensation due to peripheral neuropathy, and a lack of education results in diabetics failing to adhere to daily foot inspections as recommended. Early identification of DFUs may result in improved outcomes and reduced medical treatment costs. If DFUs are detected before they form the benefit would be even greater. Currently the best practice is to visually inspect the feet and report to a podiatrist periodically.

Temperature monitoring is a known method of predicting DFU formation. A temperature difference of 2.2° C. between similar points on opposite feet has been shown to indicate inflammation which may be a precursor to ulceration. Temperature point probes are known in the art which allow patients to take temperatures on the bottom of both feet so that temperature comparisons may be made from spot to spot. Such point probes may be used to measure skin temperature at individual target spots. If a spot on one foot demonstrates a change in temperature, compared to the same spot on the other foot, and sustains that change in temperature or higher (rises to four degrees Fahrenheit (2.2° C.) or more for two days or more) it indicates that a problem may be occurring and the patient is alerted to consult their doctor. The difficulty with this approach is that the same spot of the patients foot requires to be measured over a number of days. It is difficult for a patient to identify the same spot in order to accurately take measurements. Furthermore, the onus is on the patient to maintain a log of the temperature readings in order to do the comparisions which may result in human error. Daily visual inspection of the feet is recommended for all diabetics. As mentioned, this can be difficult due to poor vision and mobility. Current temperature monitoring devices do not facilitate the recommended daily visual inspection.

There is a need for a skin inspection device which addresses at least some of the drawbacks of the prior art.

SUMMARY

These and other problems are addressed by providing a skin inspection device for identifying abnormalities; the device comprising:
a transparent panel having an inspection area;
an array of thermochromic liquid crystal (TLC) formations provided on the transparent panel which are operable to change colour in response to a change of temperature; and
one or more image capture devices for capturing a colour image of the TLC formations and an area of skin of a target located in the inspection area; the captured colour image being analysed to identify abnormalities in the area of skin.

In one aspect, a means for identifying the formation of abnormalities based on the captured colour image is provided. Advantageously, the temperature of a target located in the inspection area is determined at multiple discrete locations.

In one aspect, a processor is operably coupled to the one or more image capture devices for controlling operations thereof.

In another aspect, a strain gauge is operable for detecting a weight bearing load on the transparent panel. Advantageously, the processor is configured to activate the image capture device in response to the strain gauge detecting a weight bearing load. In one example, the processor is configured to activate the image capture device in response to determining that the target is in a stationary position. In another example, the processor is configured to activate the image capture device in response to a target landing on a predetermined area.

In a further aspect, a housing is provided on which the transparent panel is mounted. Advantageously, the housing accommodates the processor and the one or more image capture devices therein.

In one aspect, the transparent panel provides a foot plate of sufficient strength to support the weight of an adult human.

In another apsect, the transparent panel is rigid.

In a further aspect, the transparent panel is of a resilient material operable to conforms to the shape of a sole of a foot when stepped on by an individual.

In one aspect, a backing material partially surrounds each TLC formation such that each TLC formation has an area free of the backing material.

In another aspect, the backing material is dark. Advantageously, the dark material comprises black ink. In one example; the backing material at least partially prevent external ambient light entering a viewing area.

In an exemplary arrangement, the image capture device is located beneath the transparent panel such that the area free of the backing material on each TLC is in registration with the field of view of the one or more image capture devices.

In one aspect, the TLC formations are provided on an upper surface of the transparent panel. Advantageously, the TLC formations are placed onto the transparent panel.

In a further aspect, a calibration means is provided.

In one aspect, the processor is configured to process the image captured by the image capture device for determining the temperature of the target at multiple discrete locations. In one example, multiple image capture devices are provided.

In another aspect, the processor is configured to process the image and convert the colours of the identified TLC formations into corresponding temperature values. Advantageously, the processor converts the colours of the identified TLC formations into corresponding temperature values based on a hue/saturation/lightness of the dot and a colour-temperature conversion table. In one exemplary arrangement, the processor is configured to generate a temperature map based on the temperature values. Advantageously, the processor is configured to overlay the temperature map onto the captured image of the target.

In one aspect, the processor is configured to perform image analysis on the temperature map and the captured image. Advantageously, the image analysis compares the temperature at similar points of the captured image.

In another aspect, the processor is operable to generate indicia indicative of the emergence of abnormalities. Advantageously, the processor is operable to generate indicia indicative of the emergence of ulcers.

In one aspect, the processor is operable to generate indicia indicative of the emergence of ulcers at particular locations on the captured image.

In a further aspect, the processor is configured to detect for areas on the captured images including at least one of excess callous, blisters, moisture, discolouration, and the like.

In one aspect, an alert mechanism is provided for generating an alert. Advantageously, the alert mechanism is operable to communicate the alert to a remote entity via a telecommunications network.

In one aspect, the image capture device is triggered to capture an image in response to an input. Advantageously, the image capture device is triggered to capture an image in response to a foot being placed on the target area.

In another aspect, the TLC formations are spaced at a frequency of approximately 1 per 1 $cm^2$. Advantageously, the density of TLC formations is in the range of between 0.5 and 6 per $cm^2$. In one example, each TLC formation has a diameter in the range of 0.5 mm to 5 mm.

In one aspect, the transparent panel comprises glass; a composite; polycarbonate or other plastics material.

In another aspect, one or more calibration components are provided.

In one aspect, a light source is provided.

In another aspect, a light filter is provided to alter light intensity entering a field of view of the image capture device.

In one aspect, the light source comprises one or more LEDs of a known intensity and colour.

In another aspect, one or more diffusion films are provided for reducing glare on the transparent panel.

In one aspect, a low reflection material is provided on the interior of the housing for reducing the amount of external light that is reflected onto the TLC formations.

In another aspect, foot shaped panels are provided.

In a further aspect, one or more colour calibration targets are provided.

In one aspect, the one or more calibration targets may be incorporated into the TLC formations.

In a further aspect, a plurality of image capture devices are used to capture the image of the target.

In one aspect, two or more image capture devices are provided with an area of overlap in the field of view. Advantageously, a calibration target is located in the overlap field of view.

In one aspect, a light sensor is provided within a field of view of the image capture device.

In another aspect, the output from the light sensor is used by the processor to modify the operational settings of the image capture device.

In one aspect, the output from the light sensor is used as an input by a post processing algorithm to eliminate the effects of ambient light.

In another aspect, a heat sensor is provided for sensing the temperature of the transparent panel.

In one aspect, the TLC formations are designed to operate over blue and green only. Advantageously, a black ring surrounds each TLC formation.

In another aspect, one or more baffles are configured to block at least a portion of glare-causing rays of light.

In one aspect, the one or more baffles are selectively adjustable.

In a further aspect, the dimensions, configuration, orientation or location of the one or more baffles are selectively adjustable.

These and other formations will be better understood with reference to the followings Figures which are provided to assist in an understanding of the present teaching.

BRIEF DESCRIPTION OF THE DRAWINGS

The present teaching will now be described with reference to the accompanying drawings in which:

FIG. 14 illustrates exemplary details of a skin inspection device in accordance with the present teaching.

FIG. 15 illustrates exemplary details of a skin inspection device in accordance with the present teaching.

FIG. 16 illustrates exemplary details of a skin inspection device in accordance with the present teaching.

DETAILED DESCRIPTION OF THE DRAWINGS

Figure 1:
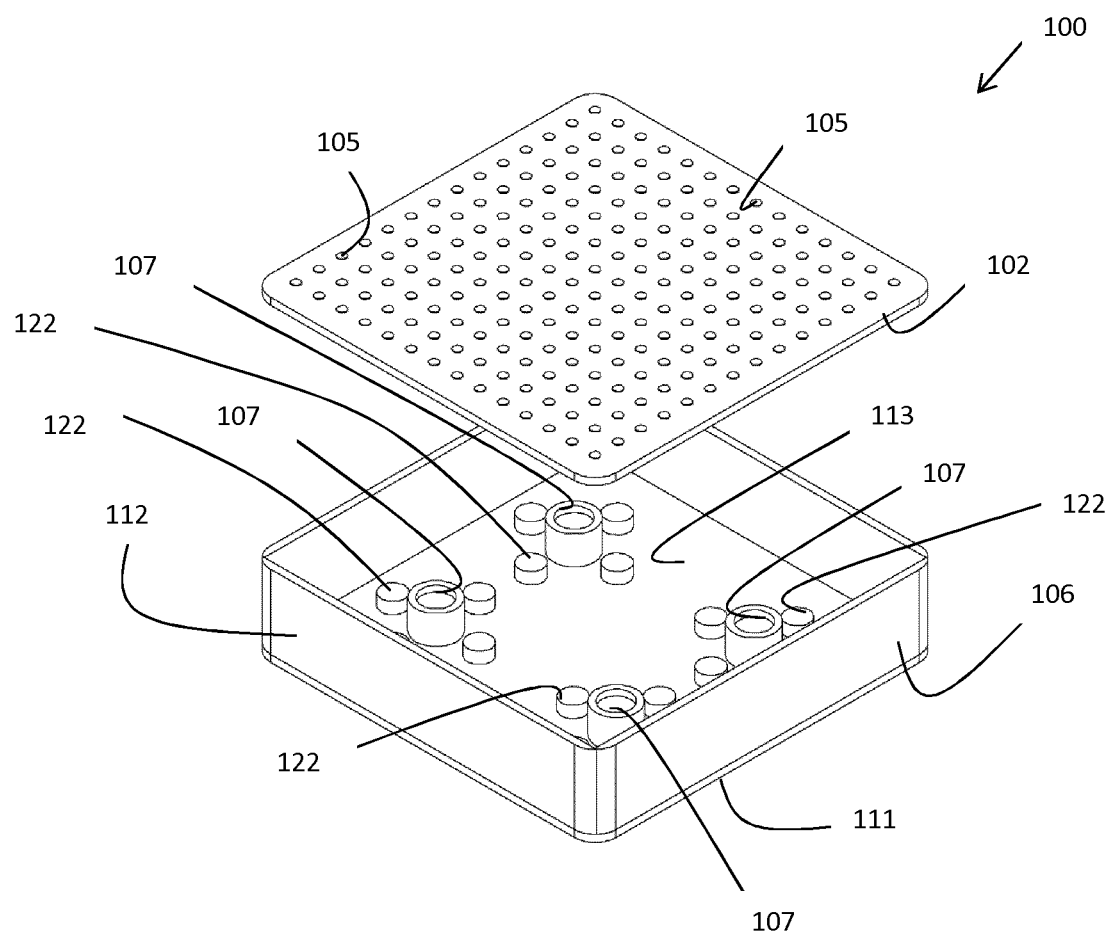
FIG. 1 illustrates a skin inspection device in accordance with the present disclosure.

The present disclosure will now be described with reference to some exemplary skin inspection devices. It will be understood that the exemplary skin inspection devices are provided to assist in an understanding of the teaching and is not to be construed as limiting in any fashion. Furthermore, elements or components that are described with reference to any one Figure may be interchanged with those of other Figures or other equivalent elements without departing from the spirit of the present teaching. It will be appreciated that for simplicity and clarity of illustration, where considered appropriate, reference numerals may be repeated among the figures to indicate corresponding or analogous elements.

Figure 2:
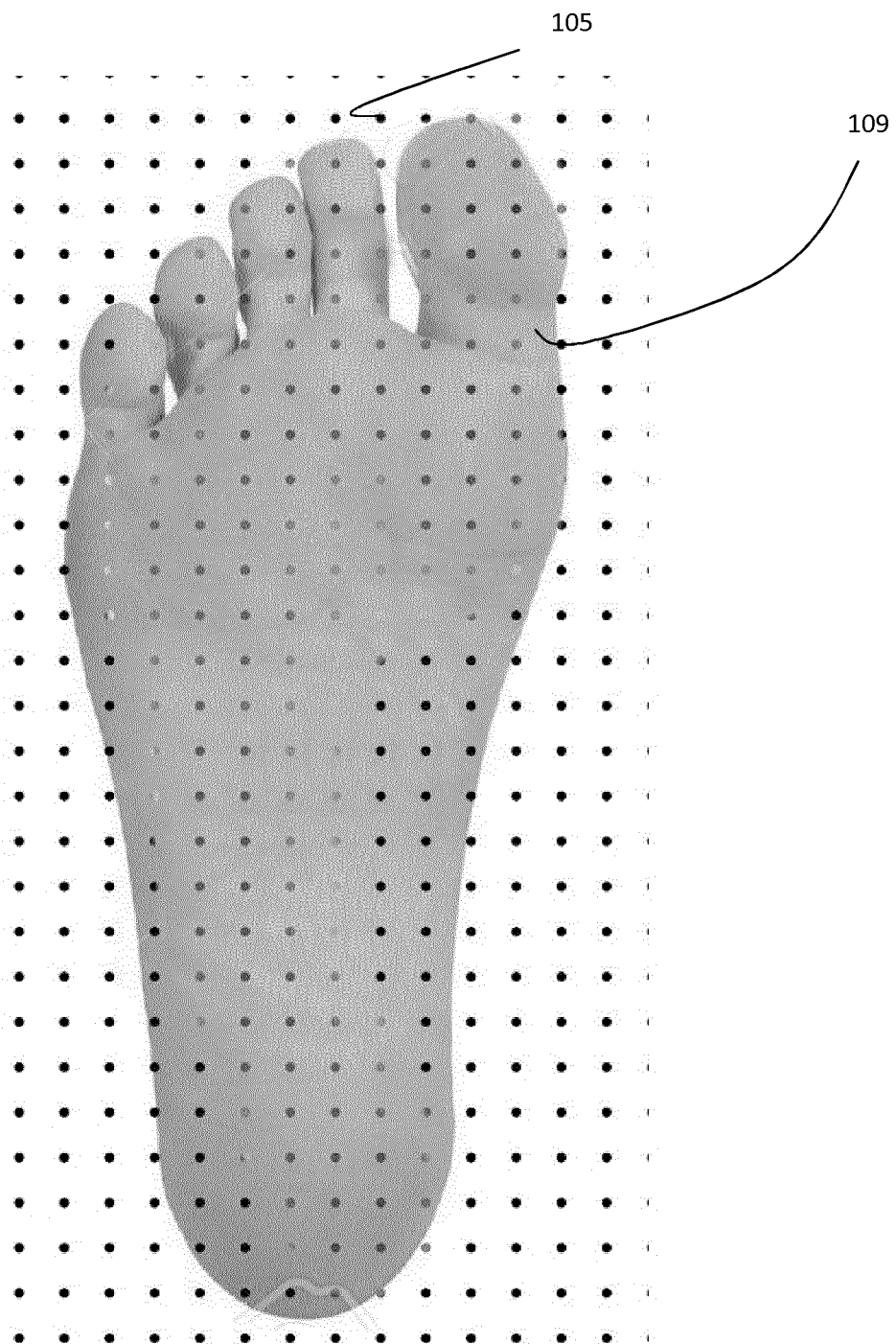
FIG. 2 is a graphical representation of a detail of the device of FIG. 1.

Referring to the drawings there is illustrated a skin inspection device 100 for identifying the formation of abnormalities in accordance with the present teaching. The device 100 comprises a transparent panel 102 which defines an inspection area for co-operating with a region of a body under inspection. For example, the region under inspection may be a foot, a hand, an arm, a leg, etc. In the exemplary arrangement, the region under inspection is a sole of a foot 109 as illustrated in FIG. 2. The transparent panel 102 provides a foot plate which accommodates the foot 109 during inspection. However, it is not intended to limit to present teaching to feet as other regions may also be inspected by the device 100. An array of thermochromic liquid crystal (TLC) formations are provided on the transparent panel 102 which are operable to change colour in response to detecting a change of temperature. The TLC formations are provided as TLC dots 105 in the exemplary embodiment. The TLC dots 105 may be spaced at a frequency of approximately 1 per 1 cm$^2$. The density of TLC dots may be in the range of between 0.5 and 6 per cm$^2$. Each TLC dot may have a diameter in the range of 0.5 mm to 5 mm. It will be appreciated that is is not intended to limit the teaching to the exempary values provided, the exemplary values are provided by way of example only.

The transparent panel 102 is supported on a housing 106 which accommodates the components of the device 100 therein. The housing 106 comprises a base 111 with side walls 112 extending upwardly therefrom which together define a hollow interior region 113. One or more image capture device 107 are provided in the hollow interior region 113 for capturing a colour image of the TLC formations and an area of skin located on the foot 109. One or more light sources in the form of LEDs 122 may also be located within the hollow interior region 113. Other types of light sources other that LEDS may be used such as cold cathode lamps, electroluminescent coated materials, for example, tapes, panels, wires, xenon or halogen bulbs. A central processing unit 115 is also provided within the hollow interior region 113 and is configured to control the operations of the device 100 as described in detail below.

Figure 3:
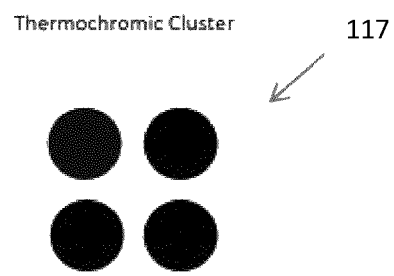
FIG. 3 is a graphical representation of a detail of the device of FIG. 1.

In the exemplary embodiment, the TLC dots 105 are provided on the transparent panel 102 by printing a pattern of TLC ink onto a top surface 114 of the transparent panel 102. It will be appreciated by those skilled in the art that the TLC dots may provided on the panel using techniques other than printing which is described by way of example only. Thermochromism is the property of a substance to change colour due to a change in temperature as is well known in the art. The TLC dots 105 are engineered to change colour at precise temperatures and are used as a way of determining foot temperature. The TLC dots 105 change colour over a predefined range, for example from red to blue over the course of a temperature range of 20° C., for example, with red being 20° C. and blue being 40° C. The temperature range required for the application of diabetic foot ulcers is 15-38° C. In one exemplary arrangement, in order to increase the hue sensitivity to temperature, while also being able to sense the full required range of 15-38° C. a number of thermochromics dots are placed side by side in a cluster 117 as best illustrated in FIG. 3. For example, the TLC dot on the top right of the cluster 117 may refer to temperatures in the range of 20-25° C. The other three TLC dots 105 are black indicating that the temperature is out of range. It is not intended to limit the configuraton of the TLC dots to a cluster arrangement which is provided by way of example only. Furthermore; it is not intended to limit the present teaching to the exemplary values provided which are provided by way of example only.

Figure 4:
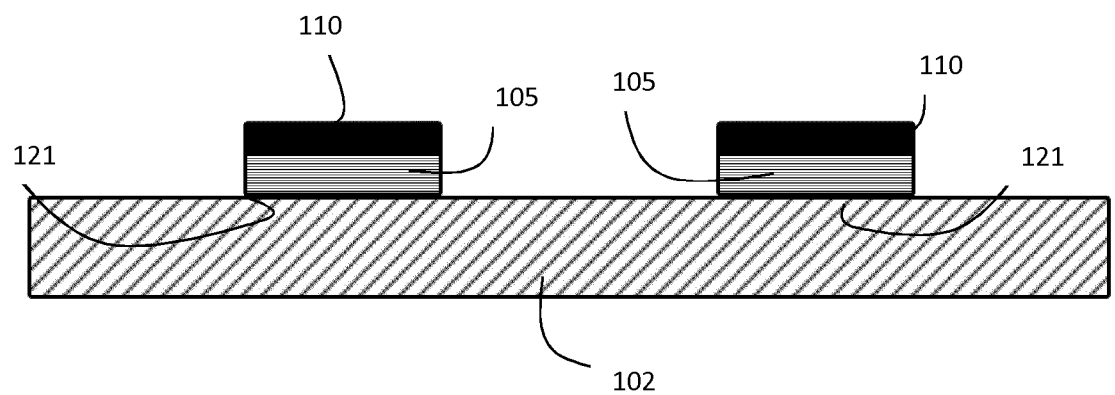
FIG. 4 is a graphical representation of a detail of the device of FIG. 1.
Figure 5A:
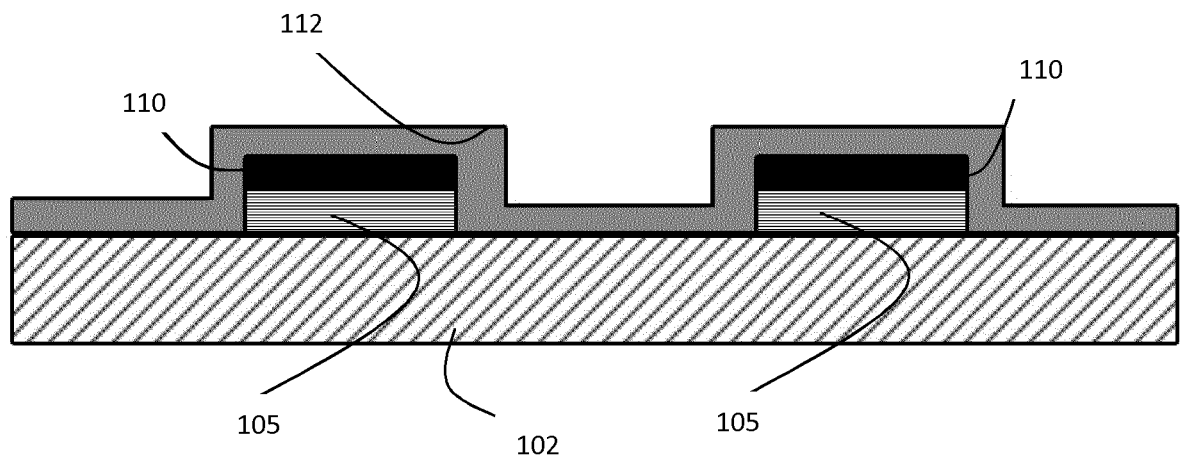
FIG. 5A is a side elevation view of a detail of the device of FIG. 1.
Figure 5B:
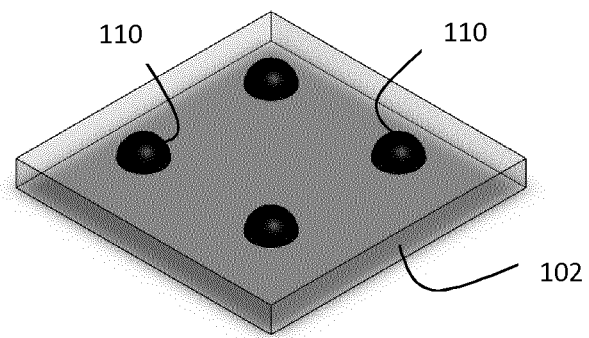
FIG. 5B is a top perspective view of a detail of the device of FIG. 1.
Figure 5C:
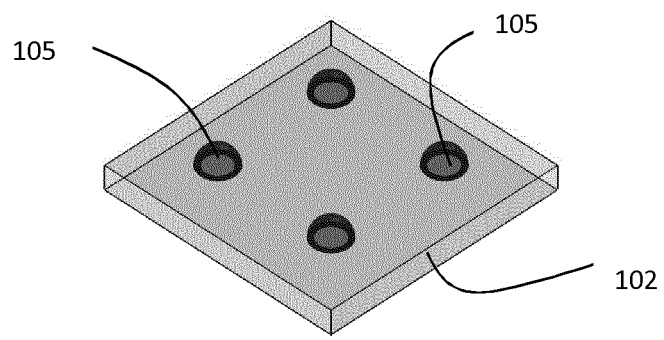
FIG. 5C is a underneath perspective view of a detail of the device of FIG. 1.
Figure 6:
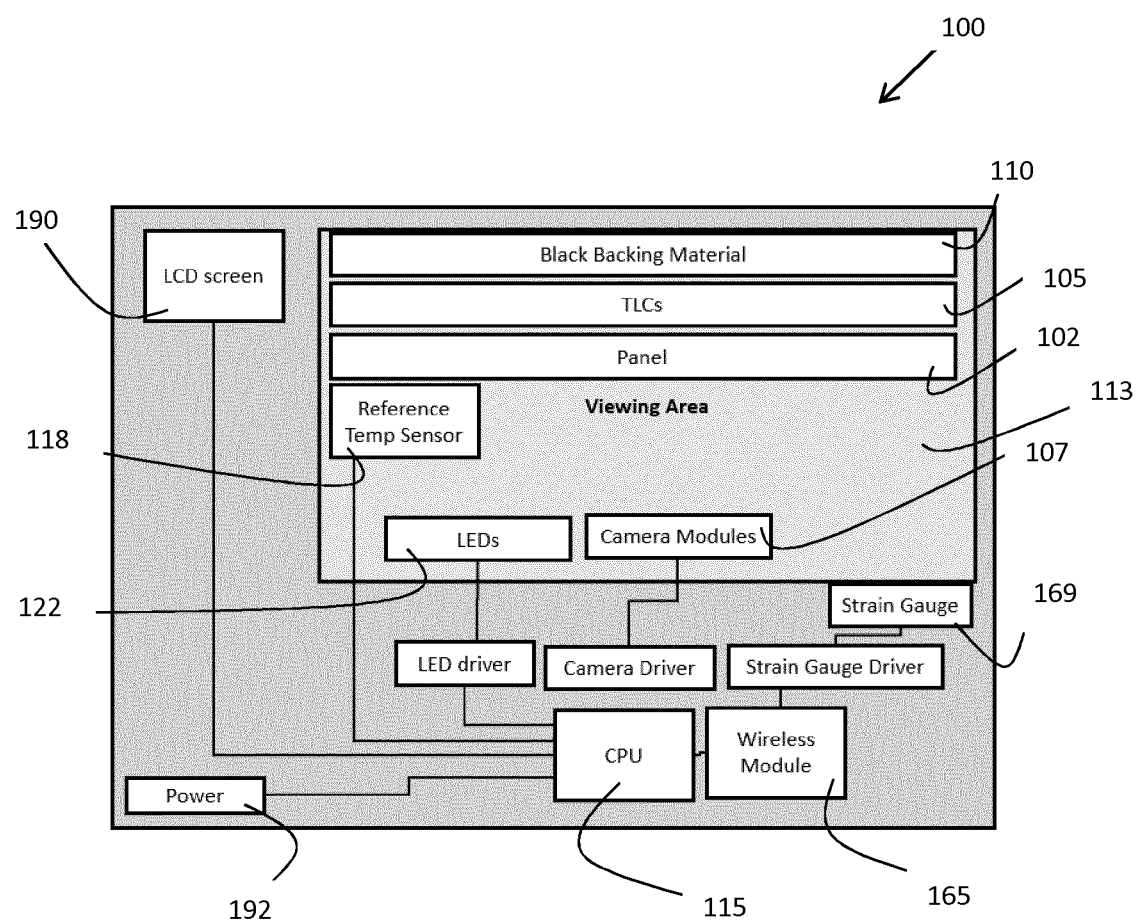
FIG. 6 is a block level diagram of details of the device of FIG. 1.

A black backing layer 110, best illustrated in FIG. 4, may be provided to cover the TLC dots 105 to improve the visibility of the colour change. A layer of TLC ink is deposited onto the transparent panel 102. The thickness of this layer may be in the region of 5-500 microns thick. A layer of black ink is then deposited onto the TLC layer with a similar thickness. The TLC and black layers may be deposited using conventional printing techniques or by using an accurate micropipette application process. The black layer may also function as an encapsulate for the TLC dots 105 protecting the TLC dots 105 from UV radiation and humidity. Both of which have been shown to result in degradation of TLC inks and reduce their longevity. The black backing layer 110 may also function to protect the TLC layer from shear and other forces. The black ink may have additional additives included to increase its resistance to UV and humidity while also increasing its strength and resistance against mechanical forces. A further transparent layer 112, best illustrated in FIG. 5A, may be placed over the TLC and black ink layers. This may take the form of a transparent plastic film which may or may not be heat treated to allow it to conform to the raised TLC dots 105 or TLC clusters 117 on the transparent panel 102. Alternatively, the transparent layer 112 may be printed onto the surface or sprayed or painted on in a way similar to what is done in the painting and coating industry. The TLC formations may be deposited on the transparent panel using any suitable technique, for example, one exemplary technique may include depositing of a black layer onto a film, layering the TLC onto the black layer and then placing the film onto the transparent panel with the TLCs located against the upper surface of the panel 102.

TLC inks will typically only accurately detect the temperature of objects that come in direct contact with it. Thus, the transparent panel is configured to have sufficient strength to support the weight of an adult human. The transparent panel 102 may be a rigid material such as glass; a composite; polycarbonate or other plastics material, or the like. As the foot 109 is a three dimensional shape with various contours, for example the arch, the entire sole of the foot 109 would not be in contact with TLC dots 105. In order to improve the contact between the TLC dots 105 and the foot 109 the panel 102 may be manufactured from a flexible or resilient material that would conform to the the shape of the sole of the foot 109. A material such as clear silicone may be used as it is both optically transparent and resilient. For example, the panel may conform to match the shape of the arch of the users foot 109. This would allow more contact with the TLC dots. In an exemplary arrangement the panel may include one or more formations for engaging with the foot in order to enhance the area of the foot that is in contact with the TCL dots. For example, the one or more formations may include one or more indentations or one or more projections or a combination of indentations and projections. It is not intended to limited the present teaching to silicone as other materials with similar properties may used as would be understood by those skilled in the art. The TLC dots 105 could then be printed onto this layer in the same fashion as outlined above.

When a rigid transparent panel 102 is used the TLC dots 105 will be located in the same XY locations relative to the image capture device 107. However, with a resilient panel 102 the TLC dots 105 may shift slightly in the X and Y directions and more dramatically in the Z direction. In this arrangement, the CPU 115 may be configured to apply an algorithm that would scan the captured image and automatically identify the dots and then convert these to temperature values.

Figure 7:
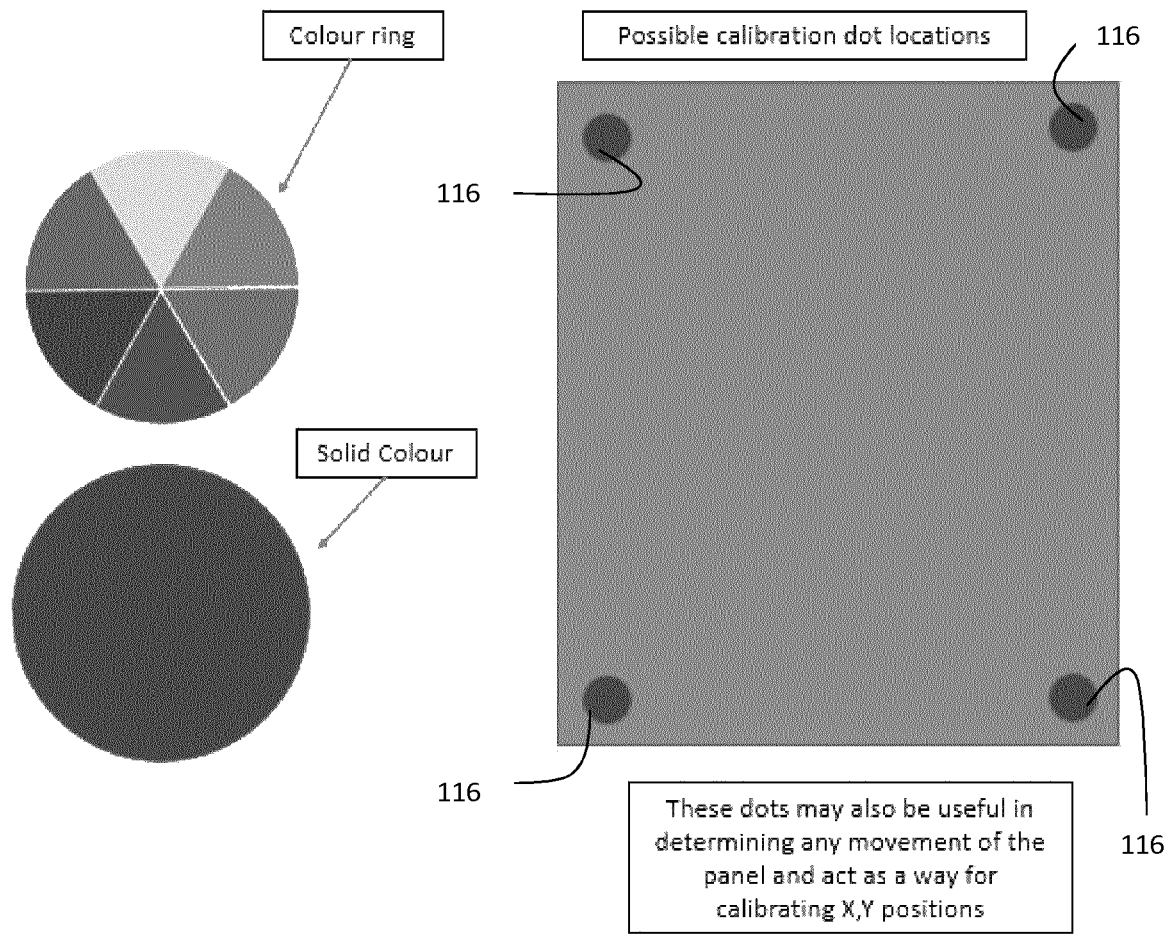
FIG. 7 is a graphical representation of a detail of the device of FIG. 1.

Various calibration features may be incorporated into the device 100 to improve accuracy. For example, temperature calibration may be achieved with the inclusion of a heat source and a TLC calibration strip. The heat source may include for example, a polyimide film heater, a ceramic heating element; or a metal heating element. The TLC calibration strip may be heated to a known value by the heat source, and the colour of the TLC calibration strip may then be analysed to confirm it is within calibration thresholds. The panel 102 may include dots 116 or features that are of a known colour as illustrated in FIG. 7. These would act as reference values to facilitate calculation of the colour of the TLC dots 105 with greater accuracy, lower processing power, cost, etc. This would assist to ensure accuracy in different lighting conditions, for example in dark and bright rooms. The panel 102 may include geo-reference features or shapes, and the location of the TLC dot array would be known with respect to these geo-references. These may act as references to facilitate the CPU 115 to identify the location of the TLC dots 105 with greater accuracy thereby lower processing power, cost, etc.

The TLC dots 105 change colour in response to heat. A digital photographic image of the TLC dots 105 is taken by the image capture device 107. The CPU 115 is configured to analyse the image of the TLC dots 105. The CPU 115 is operable to analyse for colour change and convert the colour information into temperature values. Thus the colour of the TLC dots 105 indicates the temperature at various points on the foot that are in registration with the TLC dots. If a point on one foot demonstrates a change in temperature, compared to the same point on the other foot, and sustains that change in temperature or higher (rises to four degrees Fahrenheit (2.2° C.) or more for two days or more) the CPU 115 may be configured to indicate that a DFU problem may be occurring and the patient is alerted to consult their doctor.

In order to maximise accuracy, the device 100 may include features to mitigate the effects of environmental light, light temperature and viewing angle on the captured colour. Various calibration techniques may be used to mitigate against these effects. In addition to this, various methods can be used to control the lighting environment within the hollow interior region 113 which may be considered as a "viewing area" for the image capture device 107. With the standard TLC dot 105 design there may be a risk that the CPU 115 may mistakenly identify of a portion of red skin as being red TLC dot 105 during the image analysis. To overcome this, the TLC dots 105 may be designed in such a way as to make them easy to identify. One method of achieving this would be to circle each TLC dot 105 with black backing ink. These circles would not change colour with temperature and would be easy for the CPU 115 to detect. The CPU 115 would understand that inside the circle is an area of TLC ink and the colour of this ink is related to temperature. It is not intended to limit the present teaching to TLC dots 105 having such a configuration, the exemplary TLC dots configurations are provided by way of example of how accuracy may be improved during image processing of the captured image.

The viewing area 119 within the hollow interior region 113 is the area under the transparent panel 102. The TLC dots 105 face downwards into the viewing area, as best illustrated in FIG. 4. The black backing 110 partially surrounds each TLC dot 105 such that each TLC dot 105 has an area 121 free of the backing material. The image capture device 107 faces upwardly such that the area 121 of the TLC dot 105 is within its field of view.

In a configuration where the TLC dots 105 are placed onto a transparent panel 102 made of glass, plastic or the like, it would be advantageous to know the panel temperature in order to offset for this temperature on the TLC reading. A sensor 118 may be placed on the panel 102 or a proximity IR sensor pointed at the panel could be used to obtain the panel temperature.

Figure 8A:
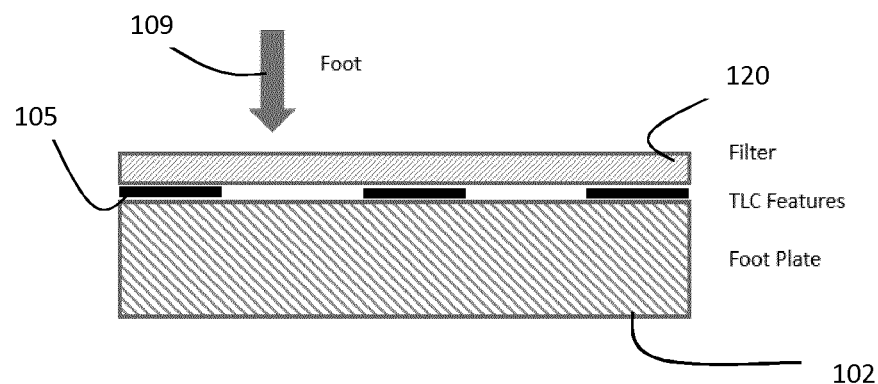
FIG. 8A illustrates another detail of a skin inspection device which is also in accordance with the present teaching.
Figure 8B:
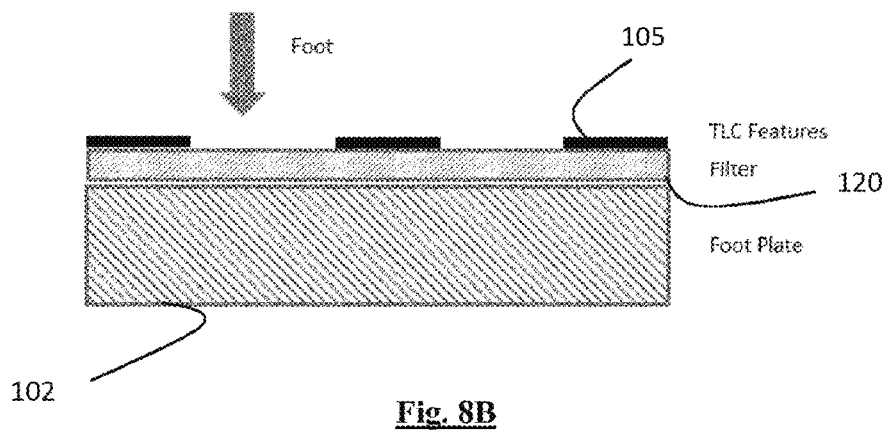
FIG. 8B illustrates another detail of a skin inspection device which is also in accordance with the present teaching.
Figure 8C:
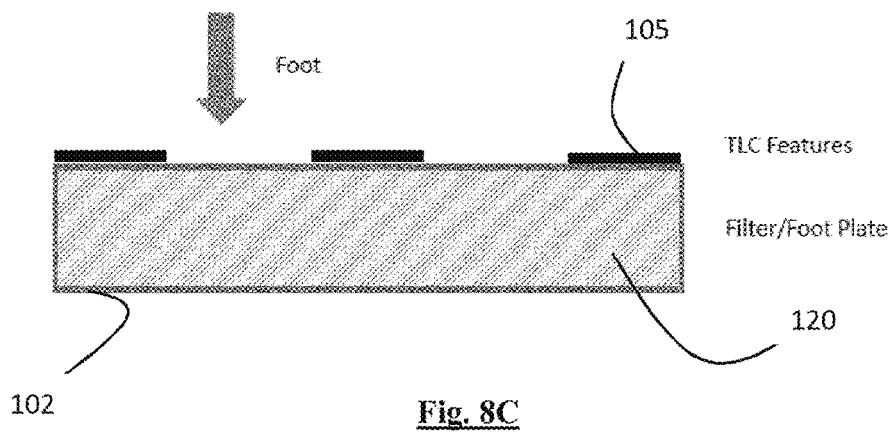
FIG. 8C illustrates another skin inspection device which is also in accordance with the present teaching.

Environmental light can change the way the image capture device 107 perceives the colour of a TLC dot 105. For example, in a bright environment the TLC dot 105 may appear to have a different hue than in a darker environment. In addition to this, the ambient light may have a slight coloration to it which may also affect the colour of the TLC dots. In order to account for these changes in environmental light, the device 100 may include means of controlling the environment. The environment within the viewing area 119 may be controlled to minimise the effect of environmental light. Referring now to FIGS. 8A-8C, a filter 120 may be used to alter the intensity of light and may also be used to filter out different colours or wavelengths of light. The filter 120 may also be used to alter the amount of UV light entering the viewing area 119 which may potentially damage the TLC material. The filter 120 may be a film placed over the panel 102, above the TLC dots 105 as illustrated in FIG. 8A. This would prevent the filter 120 from influencing the colour of the TLC dots 105 when viewed from beneath the panel 102. Alternatively, the filter 120 may be a film placed over the plate 102 and below the TLC dots 105 as illustrated in FIG. 8B. Alternatively, panel 102 may include a material with inherent filtering properties or have filtering material added to the polymer blend, removing the need for an additional filter layer as illustrated in FIG. 8C. Alternatively, the panel 102 may be coated in a filter material. Filter materials may include polarising filters, UV filters, tinted film, colour filters, or the like.

Figure 9:
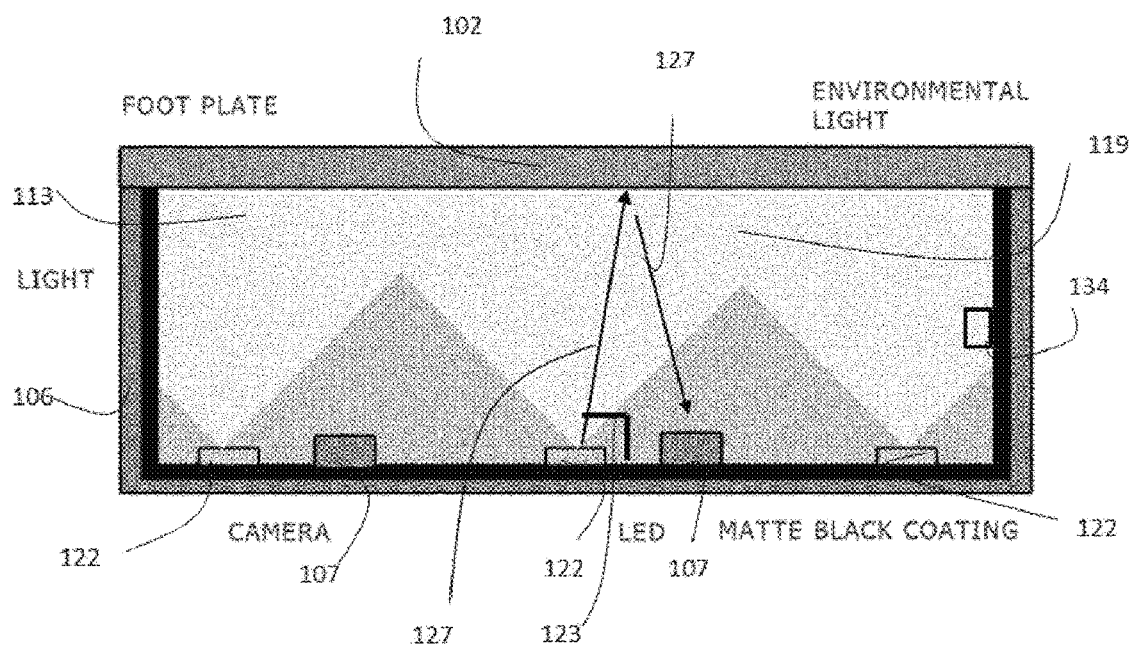
FIG. 9 illustrates another skin inspection device which is also in accordance with the present teaching.
Figure 10:
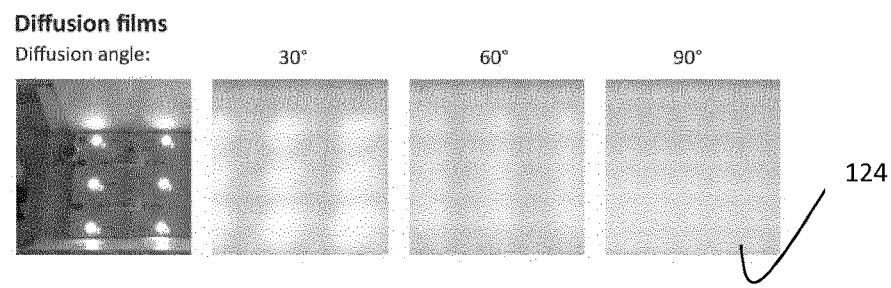
FIG. 10 illustrates a detail of the skin inspection device of FIG. 8.

A series of LEDs 122 as illustrated in FIG. 9 may be placed within the hollow interior region 113 and may act to override the environmental lighting conditions. The LEDs 122 may be of a known intensity and colour to produce repeatable conditions for viewing the TLC dots 105. In addition to standard LED lights, one or more diffusion films 124 may be provided to reduce the glare on the panel 102 coming from the LEDs 122 and to provide a uniform level of lighting across the entire surface of the panel 102. Another method of reducing this glare is to tailor the position of the target, the image capture device 107, and the illumination source. To minimise glare, the preferable arrangements are those which minimise the amount of light reflected by the illumination source onto the image capture device 107.

Another alternative method of reducing glare is to provide one or more structures such as baffle(s) 123 which block the rays of light from the illumination source 122, which will reflect directly onto the image capture device 107. The baffle 123 may be advantageously constructed in a manner which minimises the size of the shadow cast, which ensuring that the shadow is sufficiently large to block glare-causing rays of light 127. It is intended that the baffle 123 is configured to block substantially all the glare-causing rays of light 127. However in some arrangements the baffles 123 may be configured to selectively block a portion of the glare-causing rays of light 127. The baffle 123 ensures that the amount of illumination of the area where the target is located is controlled to a desired level. In this way the glare is controlled to a desired level. The location of the baffle 123 may be fixed or adjustable. A mechanism may be provided for facilitating selectively moving the baffles to desired locations. The dimensions of the baffle 123 may be fixed or adjustable. It will be appreciated that the baffle 123 may be selectively adjustable. It is envisaged that the dimensions, configuration, orientation, or location of the baffle 123 may be selectively adjustable as desired.

Figure 11:
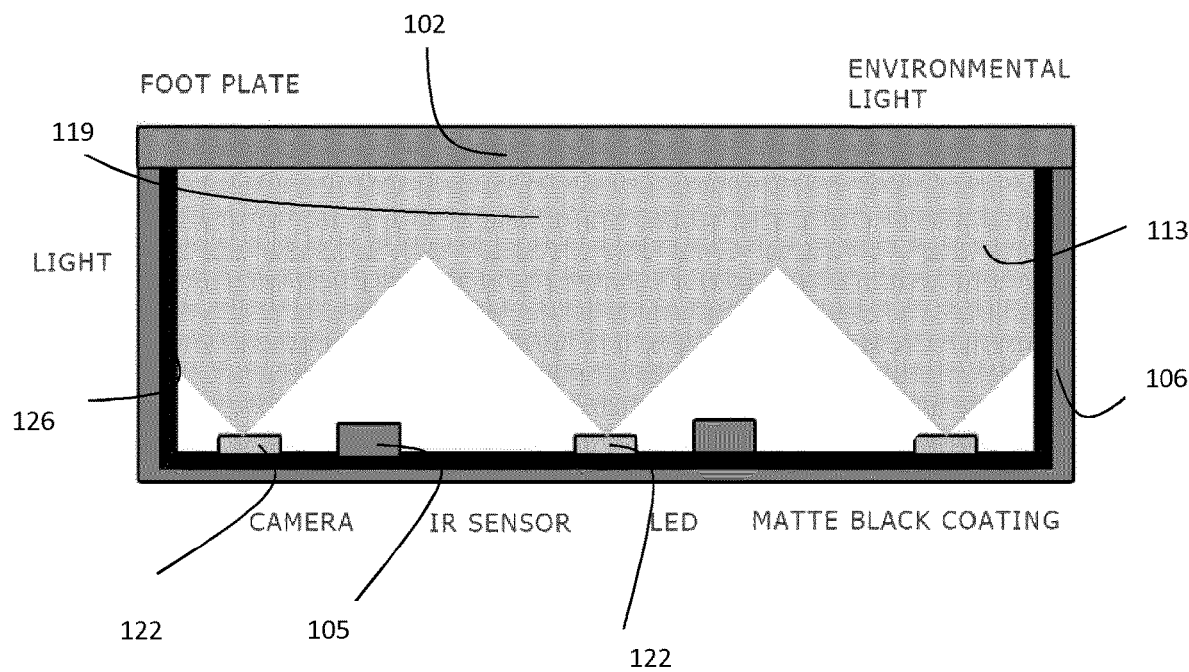
FIG. 11 illustrates another skin inspection device which is also in accordance with the present teaching.

Referring now to FIG. 11, which illustrates an exemplary skin inspecton device which is also in accordance with the present teaching. In this exemplary arrangement, all internal surfaces of the housing 106 is coated with a low reflection material 126 so that the amount of light reflected off the internal surfaces of the housing 106 is minimised. This will reduce the amount of external light that is reflected onto the TLC dots 105 from below.

Figure 12A:
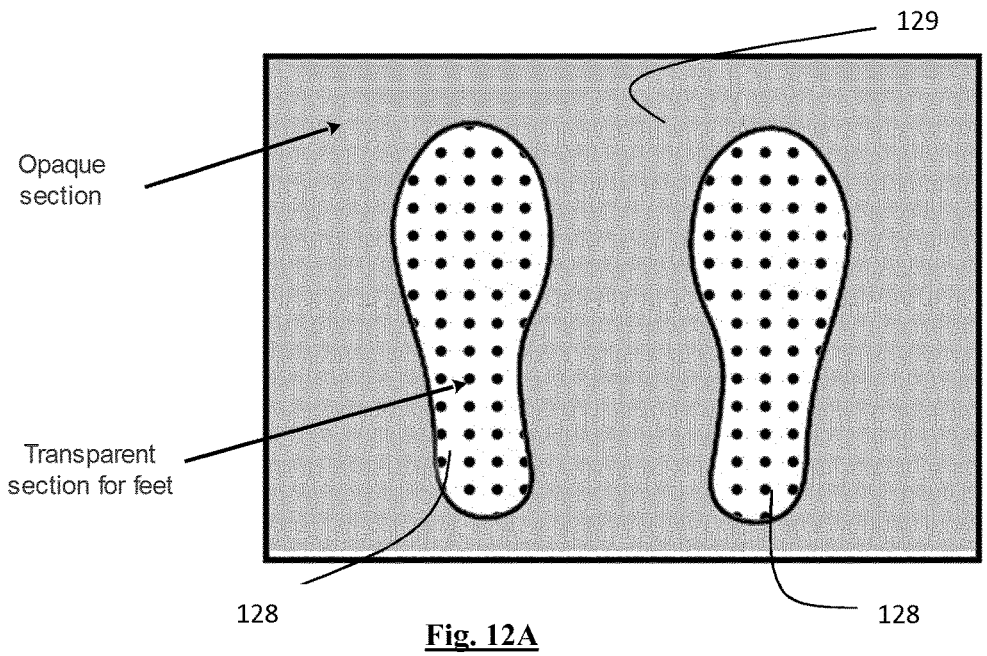
FIG. 12A illustrates exemplary details of a skin inspection device in accordance with the present teaching.
Figure 12B:
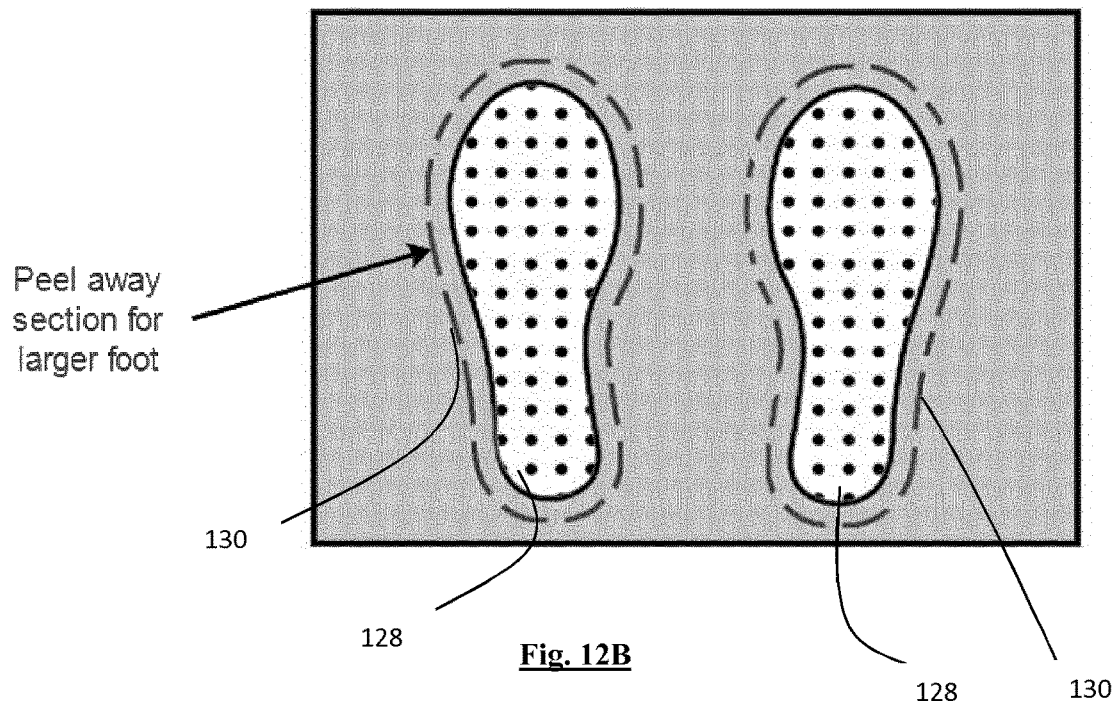
FIG. 12B illustrates exemplary details of a skin inspection device in accordance with the present teaching.

Referring now to FIGS. 12A-12B which illustrates an exemplary skin inspection device which is also in accordance with the present teaching. In order to limit the amount of environmental light entering the viewing area the user could be instructed to step into foot shaped panels 128 as opposed to a large open panel. The foot shape panels 128 may be made of a transparent material while the remaining area 129 would be opaque. The opaque area would not allow environmental light to enter the viewing area. Similarly, when the foot 109 is placed on the foot shaped panel 128 it would obstruct light from entering the viewing area. It may be beneficial for the device 100 to be stored and transported with a protective opaque cover 130. The cover 130 may have 'peel-away' sections which are of different foot sizes. The user would peel away the necessary sections to match the size of their feet. This would limit the amount of ambient light that can enter the device.

Referring to FIG. 13-16 which illustrate some exemplary optional calibration techniques which may be incorporated into the skin inspection device 100. In order to offset for different brightness and colour values it would be beneficial to provide reference colour calibration targets 132, an example would be the Macbeth Colour Checker. These calibration targets 132 would have a series of colours of know hue etc. The images taken from the image capture device 107 would include calibrations targets.

Figure 13:
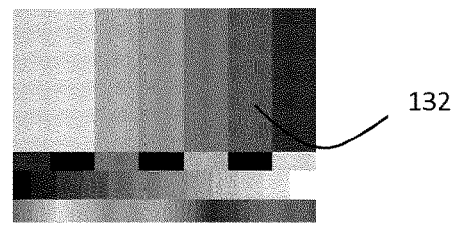
FIG. 13 illustrates an exemplary detail of a skin inspection device in accordance with the present teaching.

These calibration targets 132 may be algorithmically assessed by the CPU 115. The amount of deviation from the colours can then be used by the CPU 115 to apply a corrective offset to the captured image in order to return it to its original colour. These calibration targets 132 may be composed of an array of known colours. These targets are commonly used in applied photography applications where colour accuracy is of importance. The shape and location of these calibration targets 132 can be placed anywhere on the panel 102. Advantageously, the calibration targets would be placed in a position where they are exposed to the ambient light in a similar way to the TLC dots 105. There are a number of possible shapes for such calibration targets 132. They could be configured in the traditional way as illustrated in FIG. 13 however in this configuration they may potentially obstruct the view of the foot. To overcome this, the calibration target 132 may be placed on the corners of the panel as illustrated in FIG. 7. Alternatively, the calibration targets may be configured in a more linear strip configuration. This strip configuration could be placed along the edge of the foot plate so as not to impact on the image of the foot as illustrated in FIG. 14.

The calibration targets 132 may be incorporated into the TLC dots 105. This could potentially minimise the disruption to the photographic image of the foot 109. It may also be beneficial in that the colour calibration targets are located extremely close to the TLC dots 105 as illustrated in FIG. 15. Multiple calibration targets may be used in a multiple camera configuration device as illustrated in FIG. 16. This would enable matching the brightness and colour reproduction. Another option is to use a master slave camera configuration, to match setting across multiple cameras. Another potential configuration is to use two or more cameras with an area of overlap in the field of view, and the calibration target placed in this overlap section as illustrated in FIG. 16. The calibration target 132 could have an opaque backing, of a similar material/design as the TLC dots 105, in order to prevent ambient light from entering the device 100 through it. The material could be a black coating or could be a thin black plate/film of plastic.

A light sensor 134 may be placed within the viewing area 119 of the device 100. This light sensor 134 could detect the intensity of ambient light acting on it. One example of such a sensor is the Grove Light Sensor from Seeed Studio. This sensor can detect light intensity as well as an approximate lux value. The output from this sensor can be used by the CPU 115 to modify the image capture device 107 settings to react to the environmental light. It can also act as an input for a post processing algorithm to eliminate the effects of ambient light on TLC colour readings. The light sensor 134 could be activated by the device 100 as a photographic image is being taken.

Alternatively, the light sensor 134 could be activated prior to the user stepping on the panel 102. In this scenario the user would activate the device 100 and wait for it to perform a light intensity test before stepping onto the panel 102.

Figure 17:
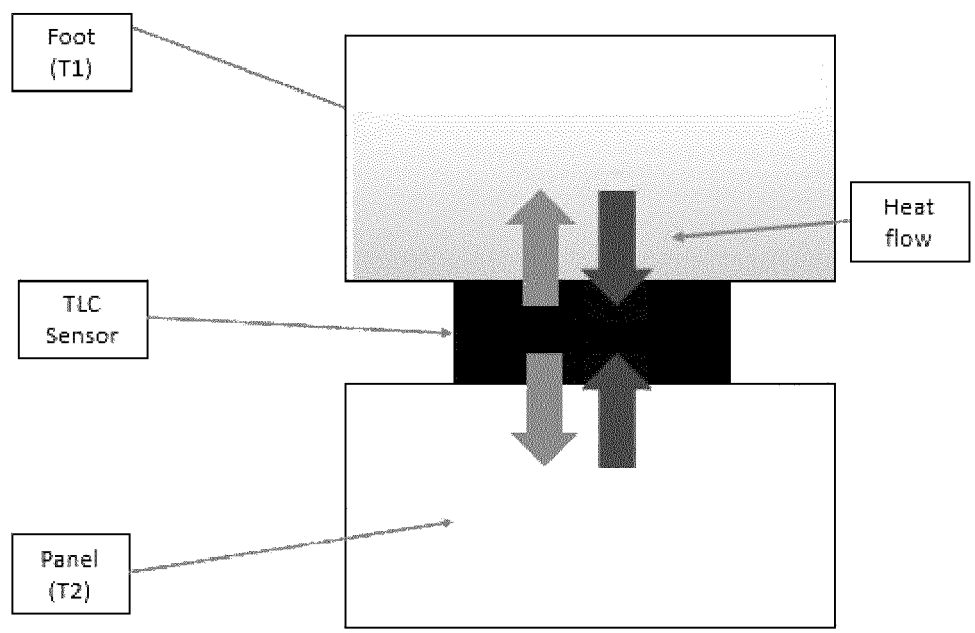
FIG. 17 illustrates exemplary details of a skin inspection device in accordance with the present teaching.

The temperature of the panel 102 could potentially impact the temperature of the TLC dots 105 to give false temperature readings. The TLC dots will be thermally acted on by the foot 109 as well as the panel 102, with the panel 102 acting to either increase or decrease the TLC temperature as illustrated in FIG. 17. In order to isolate the panel temperature 102 from the TLC temperature it is beneficial to know the temperature of the panel 102 itself. The panel temperature or reference temperature could be recorded in a number of ways. This temperature value would be input into an algorithm which would be applied to the recorded temperature values from the TLCs. This algorithm would eliminate the effect of the panel temperature on the recorded TLC temperature.

Figure 18:
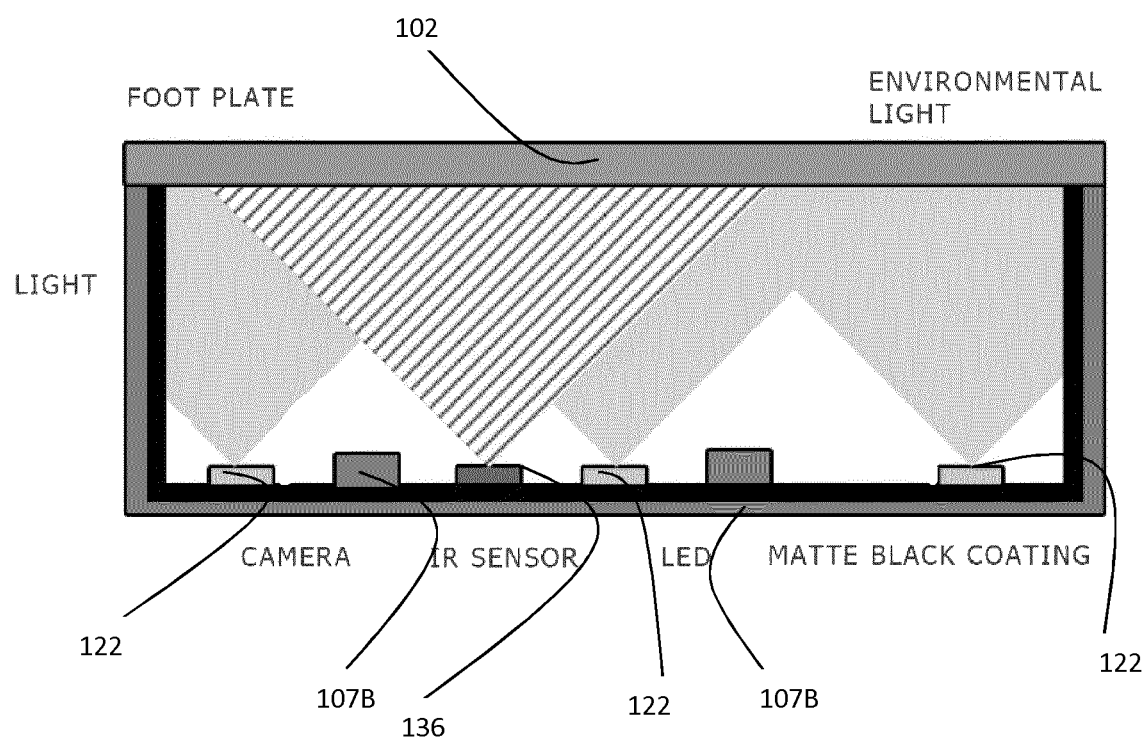
FIG. 18 illustrates exemplary details of a skin inspection device in accordance with the present teaching.
Figure 19:
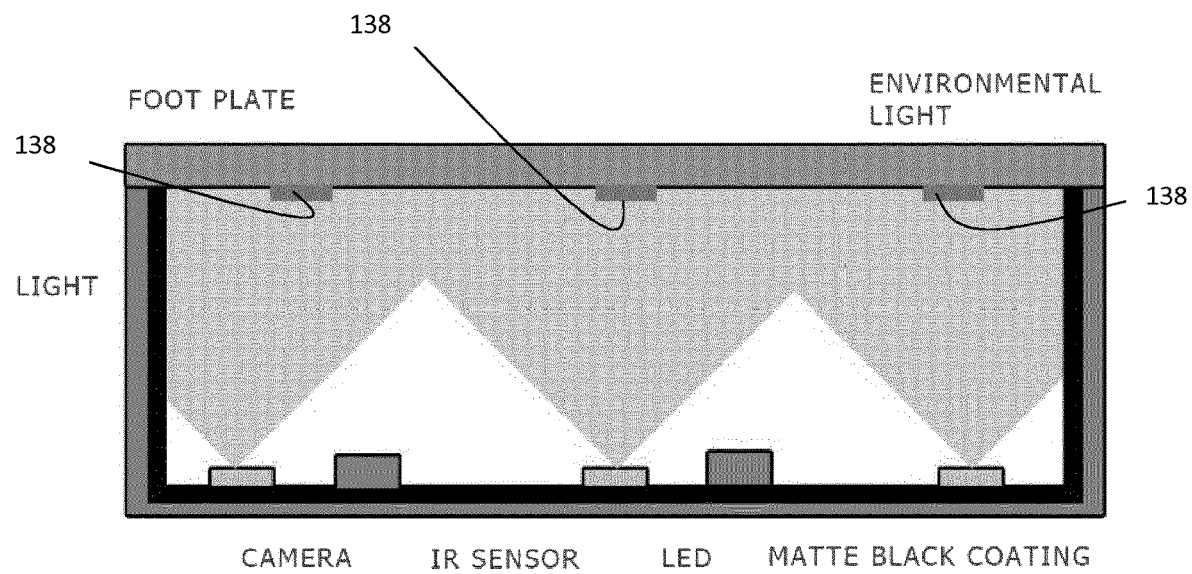
FIG. 19 illustrates another skin inspection device which is also in accordance with the present teaching.

One method uses an infrared temperature sensor pointed at the panel 102 as illustrated in FIG. 18. This would allow a relatively large area of the panel 102 to be analysed for its temperature. There may be a risk that the temperature of the panel 102 is not continuous across the entire surface. In order to determine this a number of temperature measurements can be taken by a number of temperature sensors. An alternative method of determining temperature is by using a thermistor or thermocouple that is mounted on the panel as illustrated in FIG. 19. A number of these sensors could be used to determine if the temperature of the entire panel is continuous.

Figure 20:
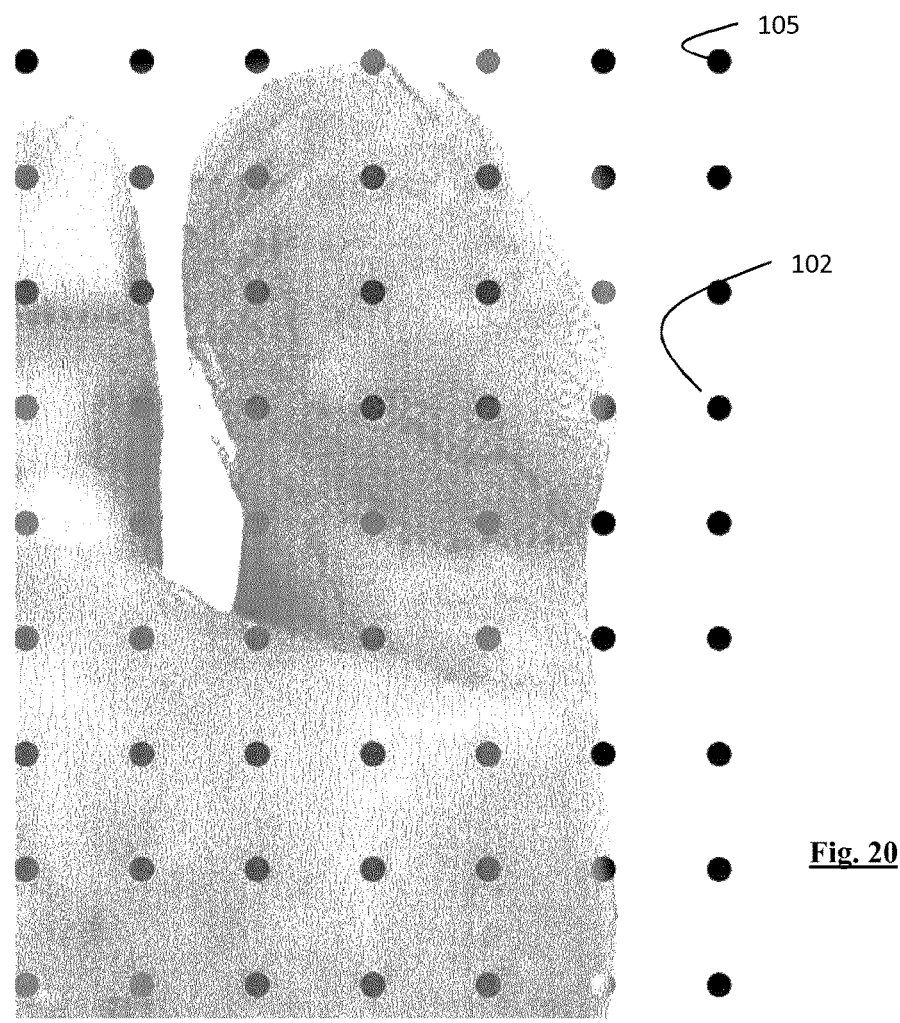
FIG. 20 illustrates exemplary details of a skin inspection device in accordance with the present teaching.
Figure 21:
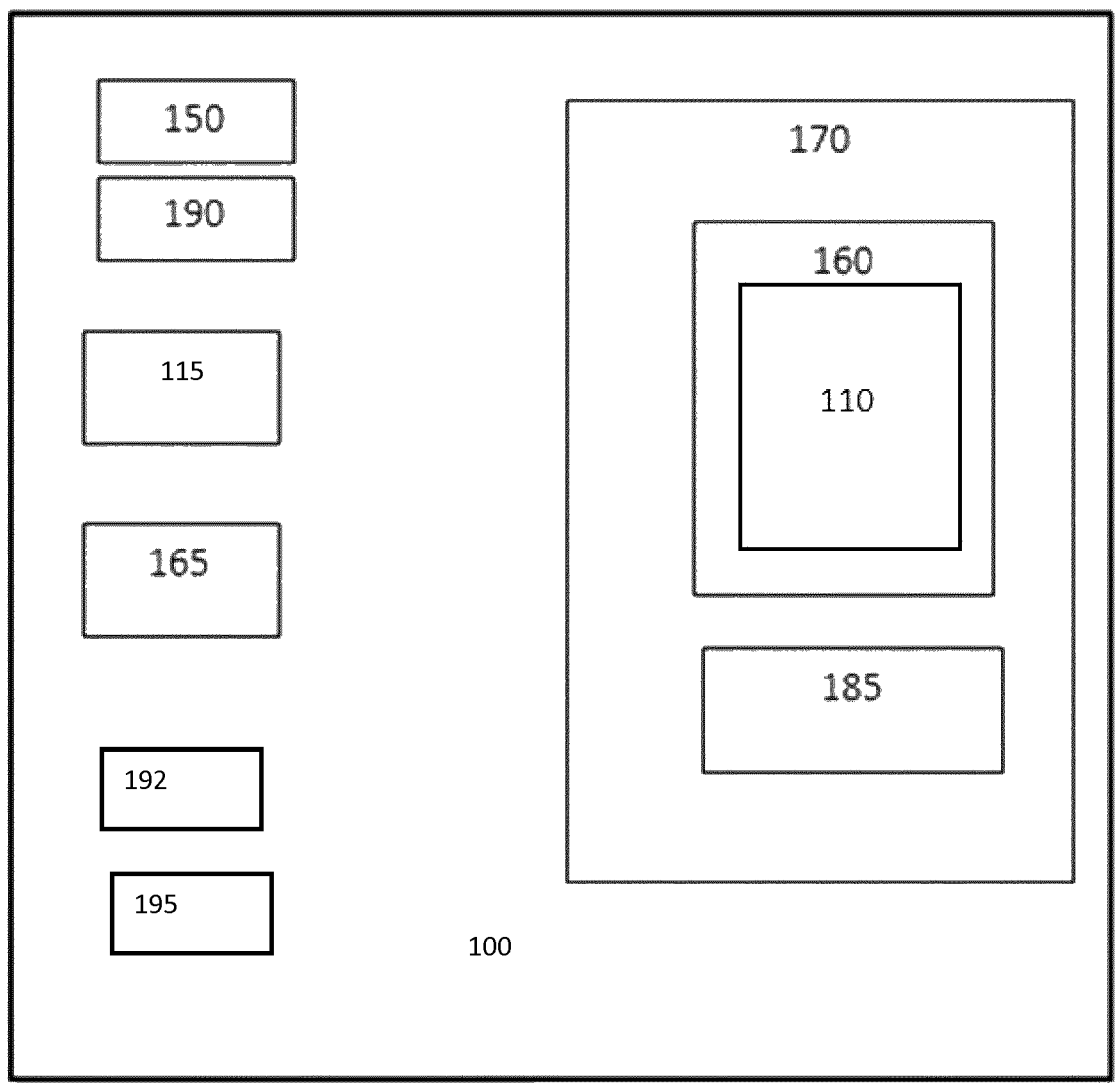
FIG. 21 illustrates exemplary components of a skin inspection device in accordance with the present teaching.
Figure 22:
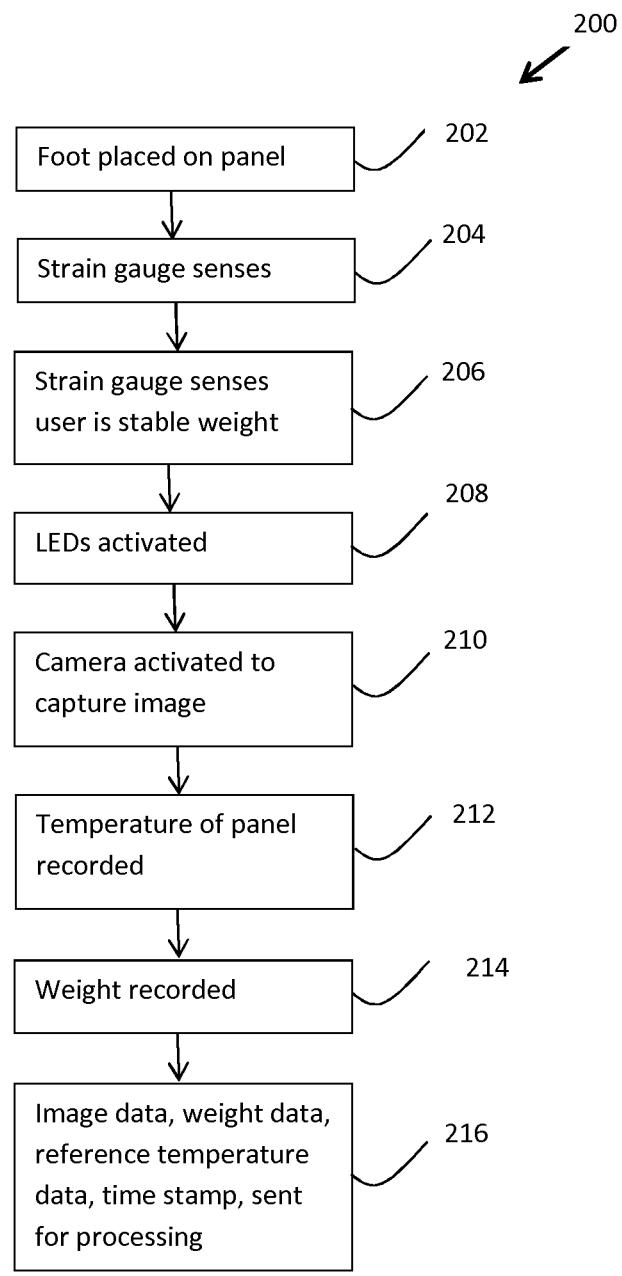
FIG. 22 is a flow chart detailing exemplary steps carried by a skin inspection device in accordance with the present teaching.

A further alternative method of recording the panel temperature could involve the use of the TLC dots themselves as illustrated in FIG. 20. The CPU 115 may apply an algorithm to identify dots which are sufficiently far from the foot. The colour of these TLC dots is proportional to the temperature of the panel. If the recorded temperature values differ significantly across the entire surface the device may alert the user that the temperature of the panel is not continuous and instruct them to move to an area where a more stable temperature can be achieved. For example, the temperature may not be continuous because the device has been left beside a radiator or in direct sunlight. Alternatively, the temperature sensors could determine that there is a constant gradient across the surface of the panel. In this case the offset applied to the recorded TLC temperatures may be based upon this gradient.

In addition to the methods described above, there could be a method whereby instead of the device being activated by the users weight it is activated by a button. Once pressed, the device 100 could take a temperature reading to determine the panel temperature. The advantage of this is that the warmth of the patients' feet will not impact this temperature reading. In addition to this temperature reading a light intensity reading may also be taken.

TLCs normally change colour over the full range of the spectrum of visible light. This may cause issues during image analysis as the colour of the foot is typically somewhere between red and yellow. This may make it more difficult for an image analysis algorithm to identify TLC dots if they are passing through the red-yellow range as they may blend into the background image of the foot. In order to overcome this the TLC dots 105 may be designed to operate over blue and green only. Alternatively, the TLC dots 105 may have a black ring around them in order for them to be easily identified by an image analysis algorithm. Use of dots as references to merge multiple images, or flatten/unfold warped images. In a multiple camera device, it will be necessary to stitch the images together after they have been captured. The dots may be used as reference points to facilitate this, as they are fixed with respect to each other, and to the cameras. For images captured with a fisheye lens, the dot may be used as reference points to unfold the image. The shape of the dots (or other shapes), and the position of these with respect to each other can be used to unfold the image.

It will be appreciated that the device 100 includes one or more software modules which are programmed to implement predefined functions. The device 100 includes various hardware and software components that function to perform the methods according to the present disclosure. The device 100 comprises a user interface 150, CPU 115 in communication with a memory 160, and a communication interface 165. The CPU 115 functions to execute software instructions that can be loaded and stored in the memory 160. The CPU 115 may include a number of processors, a multi-processor core, or some other type of processor, depending on the particular implementation. The memory 160 may be accessible by the CPU 115, thereby enabling the CPU 115 to receive and execute instructions stored on the memory 160. The memory 160 may be, for example, a random access memory (RAM) or any other suitable volatile or non-volatile computer readable storage medium. In addition, the memory 160 may be fixed or removable and may contain one or more components or devices such as a hard drive, a flash memory, a rewritable optical disk, a rewritable magnetic tape, or some combination of the above.

One or more software modules 170 may be encoded in the memory 160. The software modules 170 may comprise one or more software programs or applications having computer program code or a set of instructions configured to be executed by the processor 115. Such computer program code or instructions for carrying out operations for aspects of the systems and methods disclosed herein may be written in any combination of one or more programming languages. During execution of the software modules 170, the CPU 115 configures the device 110 to perform various operations relating to identifying the formation of skin abnormalities according to embodiments of the present disclosure. The CPU 115 may be configured to process the image captured by the image capture device 107 for determining the temperature of the target at multiple discrete locations. The CPU 115 may be operable to process the image and convert the colours of the identified TLC formations into corresponding temperature values. The CPU 115 may be programmed to convert the colours of the identified TLC formations into corresponding temperature values based on a hue/saturation/lightness of the dot and a colour-temperature conversion table. It will be appreciated by those skilled in the art that other colour spaces such as hue/saturation/value (HSV) or red, green, blue (RGB) may be used. Additionally, the CPU 115 may be configured to generate a temperature map based on the temperature values. In one exemplary arrangement, the CPU 115 is operable to overlay the temperature map onto the captured image of the target. In another arrangement, the CPU 115 is configured to perform image analysis on the temperature map and the captured image. The CPU may be programmed to compare the temperature at similar points of the captured image. The CPU 115 may be operable to generate indicia indicative of the emergence of ulcers and/or other skin abnormalities based on image analysis of the captured image. The CPU 115 may be operable to generate indicia indicative of the emergence of ulcers and/or other skin abnormalities at particular locations on the captured image. The indicia may be in the form of an output image, for example. In another example, the CPU 115 is configured to detect for areas on the captured images including at least one of excess callous, blisters, moisture, and discolouration.

Other information and/or data relevant to the operation of the present systems and methods, such as a database 185, may also be stored on the memory 160. The database 185 may contain and/or maintain various data items and elements that are utilized throughout the various operations. It should be noted that although the database 185 is depicted as being configured locally to the device 100, in certain implementations the database 185 and/or various other data elements stored therein may be located remotely. Such elements may be located on a remote device or server—not shown, and connected to the device 100 through a network in a manner known to those skilled in the art, in order to be loaded into a processor and executed.

Further, the program code of the software modules 170 and one or more computer readable storage devices (such as the memory 160) form a computer program product that may be manufactured and/or distributed in accordance with the present disclosure, as is known to those of skill in the art.

The communication interface 165 is also operatively connected to the CPU 115 and may be any interface that enables communication between the device 100 and external devices, machines and/or elements. The communication interface 165 is configured for transmitting and/or receiving data. For example, the communication interface 165 may include but is not limited to a Bluetooth, WiFi; or cellular transceiver, a wireless module, a satellite communication transmitter/receiver, an optical port and/or any other such, interfaces for connecting the device 110 to external devices.

The user interface 150 is also operatively connected to the CPU 115. The user interface may comprise one or more input device(s) such as switch(es), button(s), key(s), or a touchscreen. The user interface 150 functions to allow the entry of data. The user interface 150 functions to facilitate the capture of commands from the user such as an on-off commands or settings related to operation of the above-described method.

A display 190 may also be operatively connected to the CPU 115. The display 190 may include a screen or any other such presentation device that enables the user to view various options, parameters, and results. The display 190 may be a digital display such as an LED display. The device 110 may be powered via a power supply 192. An alert mechanism 195 is provided for generating alerts. The alert mechanism 195 is operable to communicate the alert to a remote entity via a telecommunications network.

An exemplary operation of the device 100 is described with reference to the flowcharts 200, 300A, 300B and 300C. In block 202 a user steps onto the transparent panel 102. A strain gauge 169 which is operably coupled to the CPU 115 sense the weight load on the transparent panel 102, block 204. The strain gauge 169 is configured to determine when the user is in a stable position, block 206. The CPU 115 activates the LEDs 122, block 208. In this exemplary embodiment, two image capture device 107 are activated to capture an image of the sole of the individuals foot 109 as well as the pattern of the TLC dots 105 that have changed colour to indicate the temperature of the corresponding points on the sole of the foot 109, block 210. The temperature sensor 118 records the temperature of the transparent panel 102, block 212. In this example, the skin inspection device 110 may also function as a weighing scales to capture the individual's weigh, block 214. The image data, weight data, reference temperature data, time stamp are sent to the CPU 115 for processing, step 216.

The data processing is described with reference to the flowchart 300A. The CPU 115 receives the image data, weight data, reference temperature data, time stamp, block 302. Since two image capture devices were used to capture the image data, the captured images are stitched together, block 304. The CPU 115 analyses the captured image for a colour calibration target, block 306. The CPU 115 interprets the colour calibration target and applies a colour offset to the captured image, block 308. Furthermore, the locations of the TLC dots 105 are identified by the CPU 115, block 310. The colour of the TLC dots 105 are converted to temperature values by the CPU 115, block 312. The reference temperature and offset algorithm are applied to the temperatures values by the CPU 115, block 314. The modified temperatures values are stored in a patient database, block 316. The image data, weight data, reference temperature and time stamp are also stored in the database 318. If it is determined that the temperature values indicate the formation of DFU an appropriate indicia is displayed on the display 190 alerting the individual of a potential ulceration, block 320.

An exemplary data processing approach is described with reference to the flowchart 300B. The CPU 115 receives the image data, weight data, reference temperature data, time stamp, block 302. The image data is processed by the CPU 115, block 304. This processing may include the CPU 115 applying an algorithm that would scan the captured image and identify the location of the temperature sensors 105. The locations of the temperature sensors 105 in the captured image are linked to temperature data recorded by the sensors 105, block 306. The CPU 115 generates a temperature dataset based on the recorded temperature values of the sensors 105, block 308. The temperature dataset is stored in database 185. The reference temperature and offset algorithm are applied to the temperature dataset by the CPU 115, block 310. The modified temperature dataset is stored in a patient database, block 312. The image data, weight data, reference temperature and time stamp are also stored in the database, block 314. If it is determined that the temperature values in the temperature dataset indicate the formation of DFU an appropriate indicia is displayed on the display 190 alerting the individual of a potential ulceration, block 316. It will be appreciated that it is not intended to limited the present teaching to the exemplary steps provided or to the order and sequence of the steps which may be modified as desired. For example, the inclusion of the weight data may be optional in the data processing approach described above.

Figure 23A:
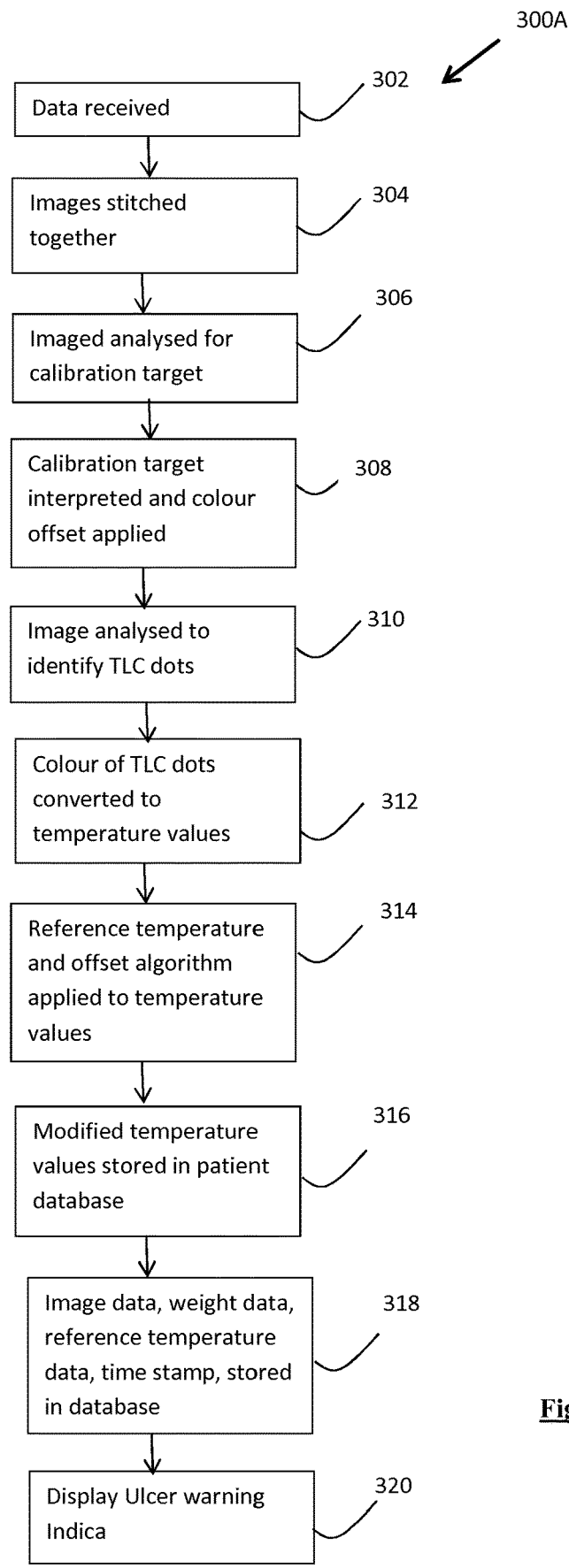
FIG. 23A is a flow chart detailing exemplary steps carried by a skin inspection device in accordance with the present teaching.
Figure 23B:
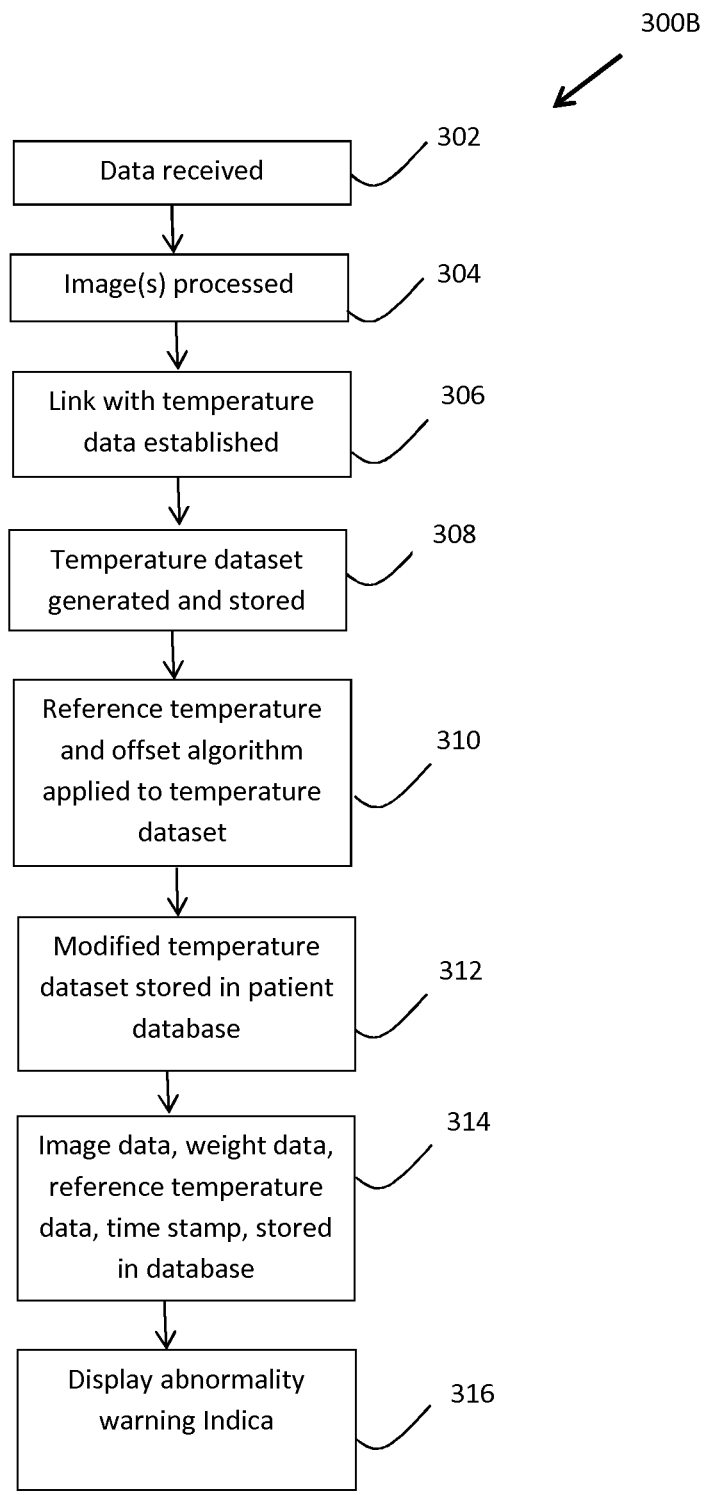
FIG. 23B is a flow chart detailing exemplary steps carried by a skin inspection device in accordance with the present teaching.
Figure 23C:
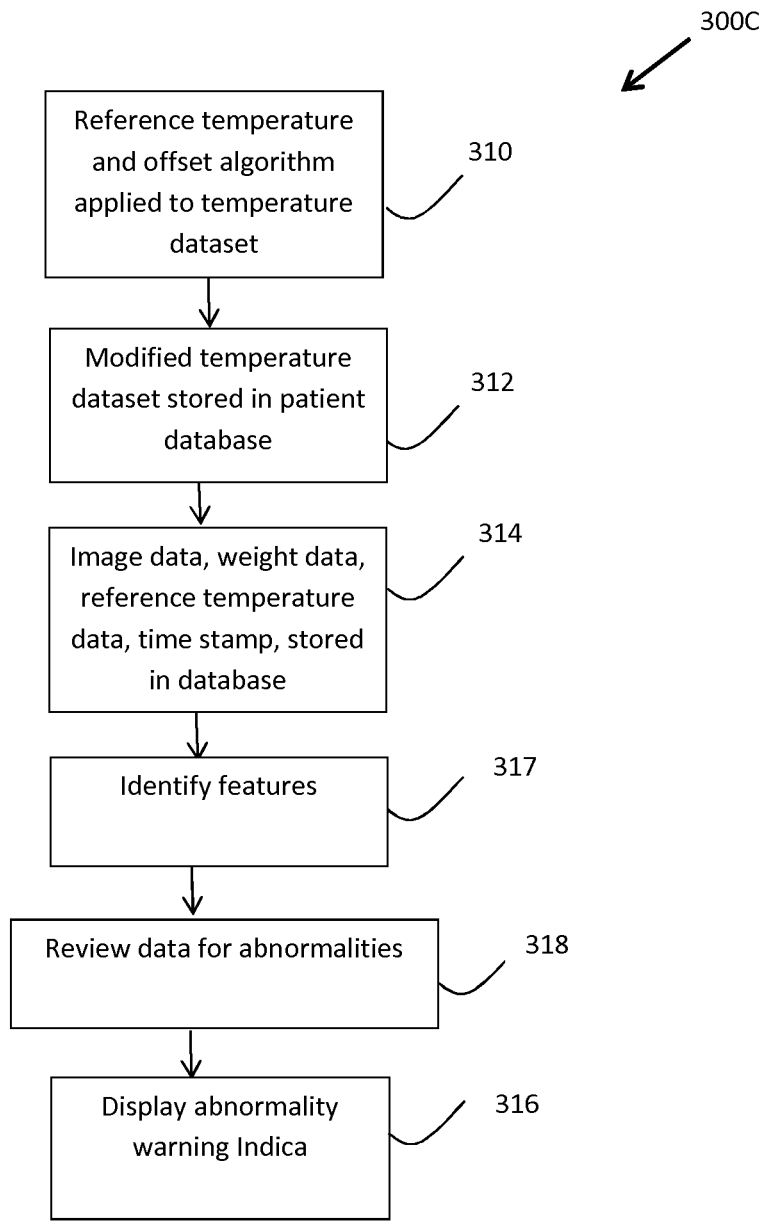
FIG. 23C is a flow chart detailing exemplary steps carried by a skin inspection device in accordance with the present teaching.

An alternative data processing approach is described with reference to the flow chart 300C. Blocks 310, 312, 314 and 316 correspond to the similarly labeled blocks in FIG. 23B. Blocks 317 and 318 describe an alternative approach. Features may be identified by various computer vision means well known to those skilled in the art, such as hue analysis, blob, corner, edge analysis and other such feature detection algorithms, block 317. Features may also be identified through comparison to a database of tagged features. A tagged dataset may also be used as a training set for a machine learning algorithm, for example using neural networks. Features may include the feet, including its size, shape, orientation etc. Other features which may be detected may include ulcers, toes, callus, discoloration, cuts, blisters, or the like.

The system may be configured to detect visual or thermal abnormalities, or a combination of both, block 318. Visual abnormalities may be detected by first identifying the feet within the image. The feet are then reviewed for abnormal features. Thermal abnormalities may be identified by using just the thermal data, or by combining the visual image with the thermal data. The location of the foot may be determined using the visual image. This is advantageous as there are occasions when the temperate of the feet is similar to ambient temperature, and hence it can be difficult to determine the location of the feet using thermal data alone. As such it can be difficult to perform comparisons between points on one foot and the other as it is difficult to determine which points to compare.

By linking the images of the feet with the temperature dataset it is possible to determine the temperature at any location on the foot. Abnormalities may be detected by comparing the temperature between like for like points on the feet (a contralateral comparison). Other methods of detecting abnormalities may include comparing the average, maximum, minimum temperature, or any other statistically generated number. Another method is to compare the data collected to previously collected data. In certain patients there may be a pre-existing temperature difference between contralateral sites, and in these instances it would be advantageous to compare the temperature to previously recorded temperatures. In another embodiment, a comparison of regional temperatures may be carried out, such as the forefoot, the heel, the hallux etc.

It is advantageous to review two different sensing modality datasets (thermal and visual) as it increases the level of information available to determine the presence of abnormalities. Some abnormalities may only be present in one of the datasets. It is advantageous as in gives four potential outcomes, whereas with a single sensing modality there are only two.

| Outcome | Thermal | Visual |
| --- | --- | --- |
| 1 | OK | OK |
| 2 | OK | Not OK |
| 3 | Not OK | OK |
| 4 | Not OK | Not OK |

The system may be configured to alter the alert based on the type of abnormalities detected. For example the indicia generated by a contralateral temperature increase without the presence of a visual abnormality may be different to the indicia generated if an active ulcer is detected.

Points in the image may be used to identify physical items such as toes, heel, arch, etc. The image may be digitised in order to generate a geometrical map of the foot. Different areas of the images may be classified based on characteristic. These classified areas may be used as reference point(s) when comparing both feet. The geometrical map may be used to identify a physical formation at a given coordinate. Thus the geometrical map allows accurate comparison to the same region on the other foot. This facilitates easy mapping data from each foot at similar points.

Figure 24A:
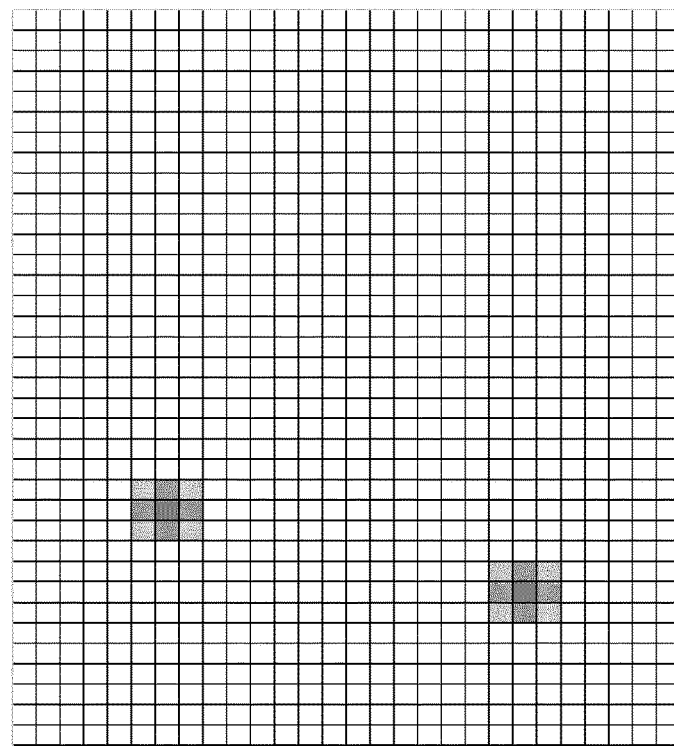
FIG. 24A is a visual representation using temperature data only.

Foot temperate is usually below body temperature. Often foot temperature can be similar temperature to ambient temperature. In such instances, it is not possible to determine where in a heat map corresponds to the foot. Hence it can be difficult to perform a contralateral temperature comparison. FIG. 24A provides an indication of a possible temperature data set which may be recorded using an array of temperature sensors 105. A significant portion of the foot is similar to ambient temperature, and hence it is not possible to distinguish from the temperature sensors 105. There are however two areas of increased temperature in the heat map. The primary mode of determining if a temperature is abnormal is to perform a contralateral comparison i.e. compare it to the same point on the other foot.

Figure 24B:
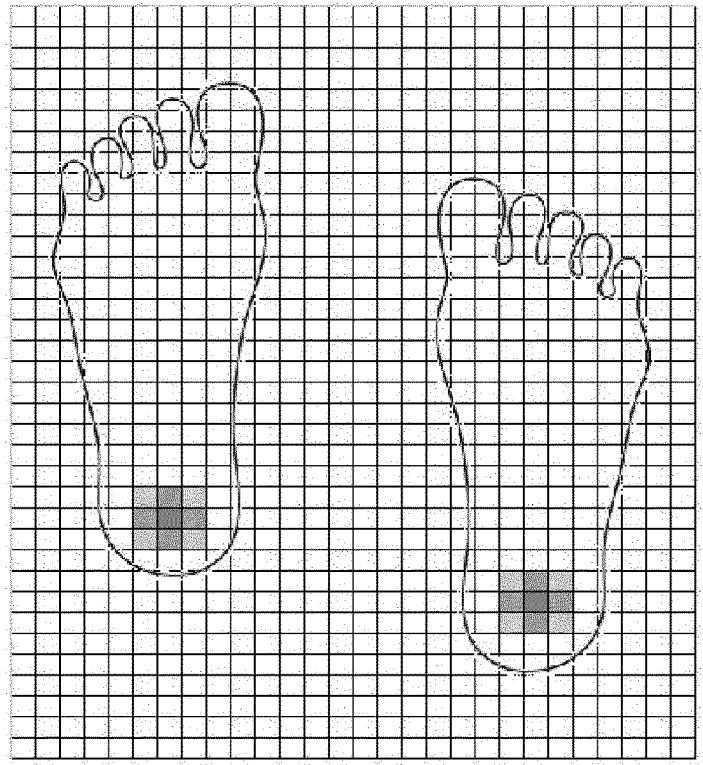
FIG. 24B is a visual representation combining temperature data and an image of a target.
Figure 24C:
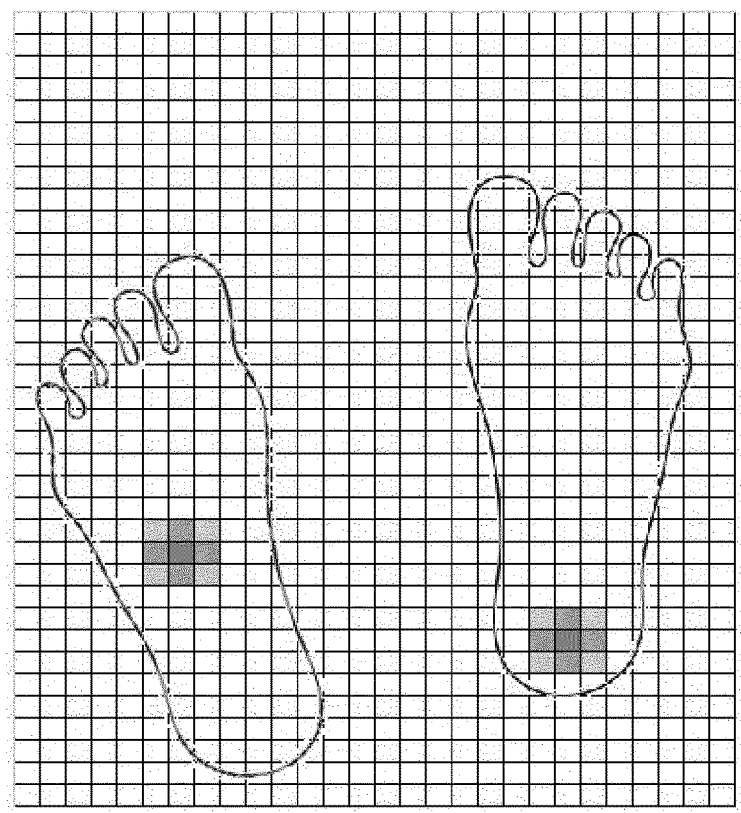
FIG. 24C is a visual representation combining temperature data and an image of a target.

FIGS. 24B and 24C indicate how the combining the datasets provides additional information which increases the usefulness of the temperature data. In FIG. 14A it is not possible to determine if the two areas of increased temperature corresponds to the same location on the feet (as demonstrated in FIG. 14B), or if they correspond to different locations (as demonstrated in FIG. 14C). The diagnosis is reversed from healthy to unhealthy based on this additional information. FIG. 14B combines temperature data with visual data and may be used to confirm that the hot spot sites correspond to same location on the foot. In a contralateral comparison, this would indicate that the temperatures are normal. FIG. 14C also combines temperature data with visual data and can be used to determine if the the hotspots are at different locations on the feet. The visual image may be used to confirm that the hot spot sites correspond to different location on the feet. In a contralateral comparison, this would indicate that the temperatures are not normal.

Figure 25:
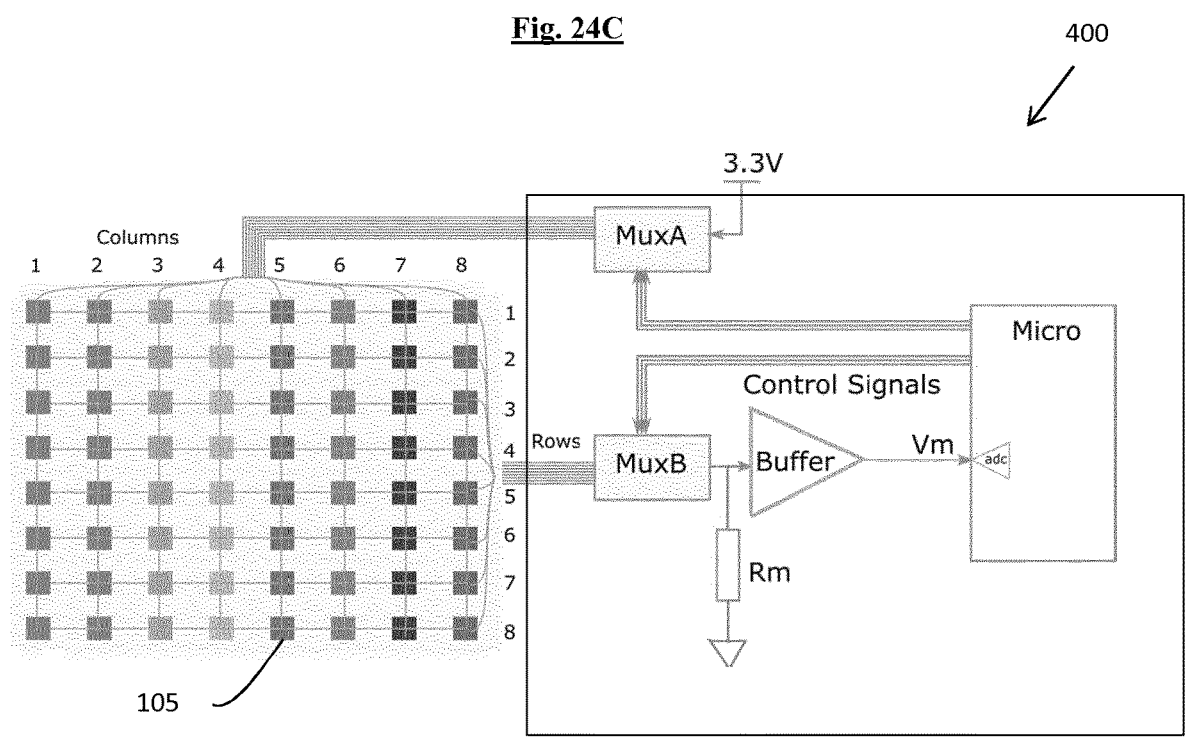
FIG. 25 illustrates an exemplary read-out circuit of a skin inspection device in accordance with the present teaching.
Figure 26:
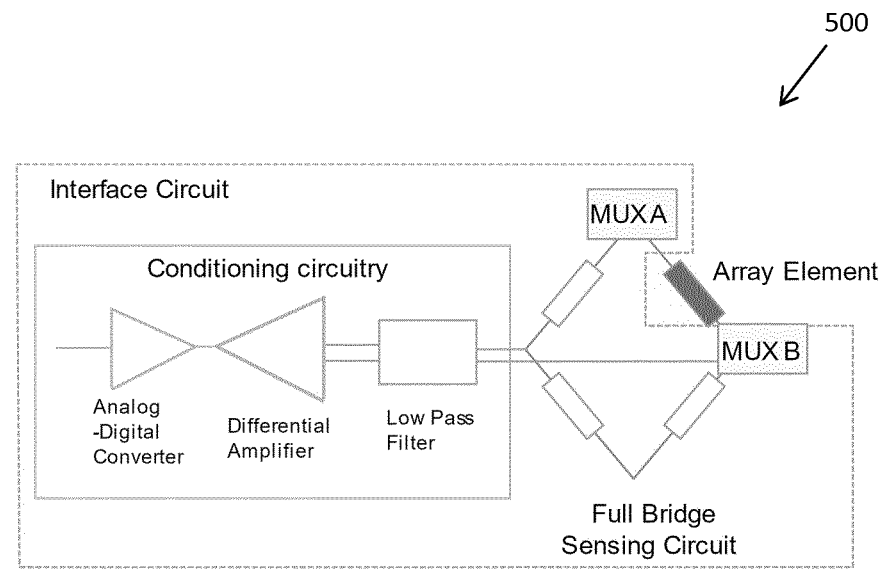
FIG. 26 illustrates another exemplary read-out circuit of a skin inspection device in accordance with the present teaching.

Referring now to FIG. 25 which illustrates an exemplary read-out circuit of a skin inspecton device in accordance with the present teaching. The read-out circuit 400 is in communication with the array of temperature sensors 105 which is shown in a matrix configuration. Temperature sensing is achieved by reading a voltage. Each element of the array of temperature sensors 105 can be individually read using two switching multiplexers, one for row selection (MuxB) and one for column selection (MuxA). The read-out circuit 400 is configured as a half-bridge circuit. An alternative embodiment of a read out circuit 500 is that of a full-bridge circuit which is shown in FIG. 26.

The maximum read speed of a single array element is a function of the multiplexer switching speed, the Analog to Digital Converter read speed and signal switching noise due to parasitic capacitances and resistances. To minimise the noise and temperature dependency of the sensing system, conditioning circuitry may be used to filter out high frequency noise using a low pass filter, amplify the signal using a differential amplifier and perform an analog to digital conversion.

Figure 27:
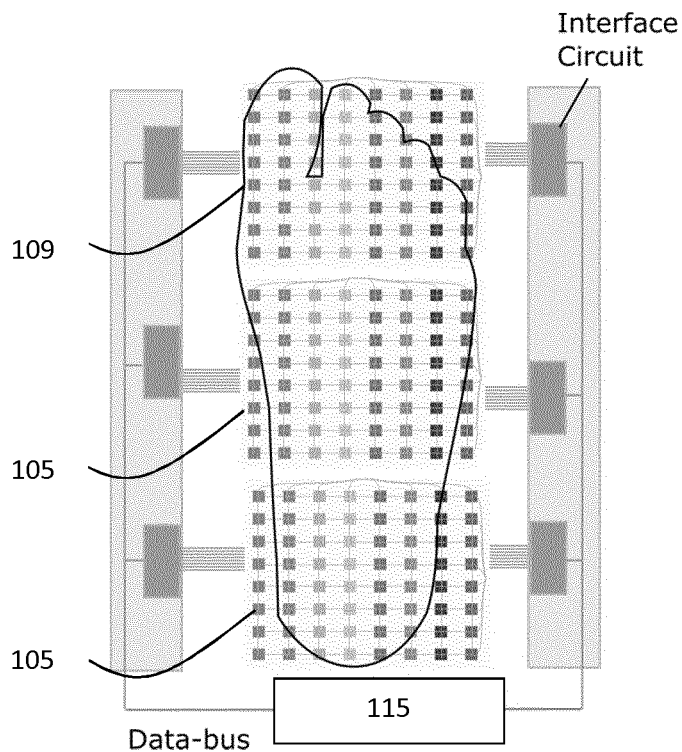
FIG. 27 illustrates exemplary details of a skin inspection device in accordance with the present teaching.

FIG. 27 illustrates exemplary read-out circuitry 400 located along the length of the foot 109 so that simultaneous sampling of the arrays of temperature sensors 105 can occur. This minimizes the overall scanning/inspection time reducing inconvenience for the user. The read-out circuitry is in communication with the CPU 115 for translating the data read from the sensors 105 into temperature values. The connection between the read-out circuitry 400, 500 and the CPU 115 may be a high speed digital bus such as I2C or SPI and the bus connections should be concealed from the field of view of the image capture device 107. The array of temperature sensors 105 are arranged in a grid with a row-column configuration. The temperature sensors 105 are spaced such that optical pathways exist between the temperature sensors 105 allowing for an image of the sole of the foot 109 in contact with the temperature sensors 105 to be captured. An optical pathway may also be defined by a zone between two or more adjacent temperature sensors 105. The temperature sensors 105 are addressable through coordinates and the coordinates of the sensors 105 may correspond to one or more pixels in the captured image. The CPU 115 is operable to map a graphical region of the sole of the foot 109 under inspection to coordinates of the temperature sensors 105.

It will be appreciated by the person of skill in the art that various modifications may be made to the above described embodiments without departing from the scope of the present invention. In this way it will be understood that the teaching is to be limited only insofar as is deemed necessary in the light of the appended claims. For ease of description, the TLC formations have been referred to as dots through out this disclosure. However, a number of different shapes may be used, for example but not limited to, circular, triangular, square, oval, pentagon, stars, chevrons, lines, curves etc. It is envisaged that the TLC formations can be provided in any desired configuration. In the exemplary arrangement; multiple image capture devices are illustrated, however, it will be appreciated that a single image capture device may be used.

An advantage of using an array of TLC dot formations is that it enables acquisition of temperature data at a high number of discrete locations, while maintaining the ability to capture a visual image of the target location. For example, the following table presents the percentage of the image obscured by TLC dots of various diameter. In the example the dots are located at a pitch of 1 cm, whereby every 100 mm$^2$ contains a single dot. The area of a circle is give by:

$$\pi \cdot r^2$$

where r is the radius of the circle

| Dot Diameter | Dot Area | Panel Transparency |
| --- | --- | --- |
| 2 mm | 3.14 mm$^2$ | 96.86% |
| 3 mm | 7.07 mm$^2$ | 92.93% |
| 4 mm | 12.57 mm$^2$ | 87.43% |

In this way, due the dispersed nature and the dimensions of the TLC dots they do not obscure a significant portion of the surface area of the sole of the foot from the view of the image capture capture device.

It will be appreciated by the person of skill in the art that various modifications may be made to the above described embodiments without departing from the scope of the present invention. In this way it will be understood that the teaching is to be limited only insofar as is deemed necessary in the light of the appended claims. In an exemplary embodiment; the skin inspection device 100 may be incorporated into a weighing scale which would have a means for calculating the weight of an individual.

Similarly the words comprises/comprising when used in the specification are used to specify the presence of stated formations, integers, steps or components but do not preclude the presence or addition of one or more additional formations, integers, steps, components or groups thereof.

The invention claimed is:

1. A skin inspection device for identifying skin abnormalities; the device comprising:
    a transparent panel having an inspection area;
    an array of discrete thermochromic liquid crystal (TLC) formations provided on a top surface of the transparent panel which are operable to change colour in response to a change of temperature of the TLC formations;
    one or more image capture devices for a combined capture of a colour image of the TLC formations and an image of a target of an area of skin of a patient's foot located in the inspection area such that a combined colour image is provided, wherein the combined colour image provides a dataset combining corresponding temperature values with co-located image data of both the target of the area of the skin and the TLC formations; and
    a processor operably coupled to the one or more image capture devices for controlling operations thereof,
    wherein the processor is operable to generate indicia indicative of an emergence of ulcers and/or the skin abnormalities, and
    wherein the TLC formations are spaced apart from each other such that, when a subset of the TLC formations change colour in response to the change of temperature of the subset of the TLC formations, portions of the transparent panel between adjacent TLC formations of the subset changing colour remain transparent, distances between peripheries of the TLC formations being greater than a diameter of the TLC formations, the co-located image data being addressable through coordinates and the coordinates of the co-located image data correspond to one or more pixels in the combined colour image, the processor being operable to map a graphical region of the area of the skin to the coordinates of the co-located image data.

2. A skin inspection device as claimed in claim 1, further comprising a strain gauge operable for detecting a weight bearing load on the transparent panel.

3. A skin inspection device as claimed in claim 2, wherein the processor is configured to activate the one or more image capture devices in response to the strain gauge detecting the weight bearing load.

4. A skin inspection device as claimed in claim 1, further comprising a housing on which the transparent panel is mounted.

5. A skin inspection device as claimed in claim 4, wherein the housing accommodates the processor and the one or more image capture devices therein.

6. A skin inspection device as claimed in claim 4, further comprising a low reflection material on an interior of the housing for reducing an amount of external light that is reflected onto the TLC formations.

7. A skin inspection device as claimed in claim 1, wherein the transparent panel provides a foot plate of sufficient strength to support a weight of the patient in a form of an adult human.

8. A skin inspection device as claimed in claim 1, wherein the transparent panel is rigid.

9. A skin inspection device as claimed in claim 1, wherein the transparent panel is of a resilient material operable to conform to a shape of a sole of the foot when stepped on by the patient.

10. A skin inspection device as claimed in claim 1, wherein a backing material partially surrounds each TLC formation such that each TLC formation has an area free of the backing material.

11. A skin inspection device as claimed in claim 10, wherein the backing material is dark.

12. A skin inspection device as claimed in claim 11, wherein the dark material comprises black ink.

13. A skin inspection device as claimed in claim 10, wherein the one or more image capture devices are located beneath the transparent panel such that the area free of the backing material of each TLC formation is in a field of view of the one or more image capture devices.

14. A skin inspection device as claimed in claim 1, wherein the TLC formations are printed onto the transparent panel.

15. A skin inspection device as claimed in claim 1, further comprising a calibration means.

16. A skin inspection device as claimed in claim 1, wherein the processor is configured to process the combined colour image captured by the one or more image capture devices for determining a temperature of the target of the area of the skin of the patient's foot at multiple discrete locations.

17. A skin inspection device as claimed in claim 1, wherein the processor converts the combined colour image of the TLC formations into the corresponding temperature values based on a hue/saturation/lightness of the TLC formations and a colour-temperature conversion table.

18. A skin inspection device as claimed in claim 17, wherein the processor is configured to generate a temperature map based on the corresponding temperature values.

19. A skin inspection device as claimed in claim 18, wherein the processor is configured to overlay the temperature map onto the combined colour image of the target of the area of the skin of the patient's foot.

20. A skin inspection device as claimed in claim 18, wherein the processor is configured to perform image analysis on the temperature map and the combined colour image.

21. A skin inspection device as claimed in claim 20, wherein the image analysis compares the corresponding temperature values at corresponding points on the patient's foot and opposite foot of the combined colour image.

22. A skin inspection device as claimed in claim 1, wherein the processor is operable to generate the indicia indicative of the emergence of ulcers and/or the skin abnormalities at particular locations on the combined colour image.

23. A skin inspection device as claimed in claim 1, wherein the processor is configured to detect for areas on the combined colour image including at least one of excess callus, blisters, moisture, and discolouration.

24. A skin inspection device as claimed in claim 1, further comprising an alert mechanism for generating an alert.

25. A skin inspection device as claimed in claim 24, wherein the alert mechanism is operable to communicate the alert to a remote entity via a telecommunications network.

26. A skin inspection device as claimed in claim 1, wherein the system is configured to trigger the one or more image capture devices to capture the colour image of the TLC formations and the image of the target of the area of the skin in response to an input.

27. A skin inspection device as claimed in claim 1, wherein the system is configured to trigger the one or more image capture devices to capture the colour image of the TLC formations and the image of the target of the area of the skin in response to the patient's foot being placed on the inspection area.

28. A skin inspection device as claimed in claim 1, wherein the TLC formations are spaced at a frequency of 1 per 1 cm$^2$.

29. A skin inspection device as claimed in claim 1, wherein a density of TLC formations is in a range of between 0.5 and 6 per cm$^2$.

30. A skin inspection device as claimed in claim 1, wherein each TLC formation has a diameter in a range of 0.5 mm to 4 mm.

31. A skin inspection device as claimed in claim 1, wherein the transparent panel comprises glass, a composite material, polycarbonate, or other plastics material.

32. A skin inspection device as claimed in claim 1, further comprising one or more calibration components.

33. A skin inspection device as claimed in claim 1, further comprising a light source.

34. A skin inspection device as claimed in claim 33, wherein the light source comprises one or more LEDs of a known intensity and colour.

35. A skin inspection device as claimed in claim 1, further comprising a light filter to alter light intensity entering a field of view of the one or more image capture devices.

36. A skin inspection device as claimed in claim 1, further comprising one or more diffusion films for reducing glare on the transparent panel.

37. A skin inspection device as claimed in claim 1, further comprising foot shaped panels.

38. A skin inspection device as claimed in claim 1, further comprising one or more colour calibration targets.

39. A skin inspection device as claimed in claim 38, wherein the one or more calibration targets are incorporated into the TLC formations.

40. A skin inspection device as claimed in claim 1, wherein two or more of the one or more image capture devices are provided with an area of overlap in a field of view.

41. A skin inspection device as claimed in claim 40, wherein, a calibration target is located in the area of overlap.

42. A skin inspection device as claimed in claim 1, further comprising a light sensor within a field of the one or more image capture devices.

43. A skin inspection device as claimed in claim 42, wherein the system is configured such that output from the light sensor is used by the processor to modify operational settings of the one or more image capture devices.

44. A skin inspection device as claimed in claim 42, wherein the system is configured such that output from the light sensor is used as an input by a post processing algorithm in the processor to eliminate effects of ambient light.

45. A skin inspection device as claimed in claim 1, further comprising a heat sensor for sensing a temperature of the transparent panel.

46. A skin inspection device as claimed in claim 1, wherein the TLC formations are designed to operate over a blue and green range of a visible light spectrum.

47. A skin inspection device as claimed in claim 1, further comprising a black ring surrounding each TLC formation.

48. A skin inspection device as claimed in claim 1, further comprising one or more baffles configured to block at least a portion of glare-causing rays of light.

49. A skin inspection device as claimed in claim 48, wherein the one or more baffles are selectively adjustable.

50. A skin inspection device as claimed in claim 49, wherein dimensions, configuration, orientation or location of the one or more baffles are selectively adjustable.

51. A weighing scale comprising a skin inspection device as claimed in claim 1; and a means for calculating a weight of the patient.

* * * * *